US012758091B2

(12) United States Patent
Fridman et al.

(10) Patent No.: US 12,758,091 B2
(45) Date of Patent: Oct. 13, 2026

(54) INTRAORAL SCANNING SYSTEM COMPONENT PAIRING

(71) Applicant: Align Technology, Inc., San Jose, CA (US)

(72) Inventors: Edi Fridman, Rishon le Zion (IL); Moshe Alboher, Tsoran (IL)

(73) Assignee: Align Technology, Inc., San Jose, CA (US)

( * ) Notice: Subject to any disclaimer, the term of this patent is extended or adjusted under 35 U.S.C. 154(b) by 56 days.

(21) Appl. No.: 18/770,509

(22) Filed: Jul. 11, 2024

(65) Prior Publication Data

US 2025/0025035 A1 Jan. 23, 2025

Related U.S. Application Data

(60) Provisional application No. 63/514,529, filed on Jul. 19, 2023.

(51) Int. Cl.
*G16H 10/60* (2018.01)
*A61B 1/00* (2006.01)
(Continued)

(52) U.S. Cl.
CPC ............ *A61B 1/24* (2013.01); *A61B 1/00016* (2013.01); *A61B 1/00045* (2013.01);
(Continued)

(58) Field of Classification Search
CPC ... A61B 1/24; A61B 1/00016; A61B 1/00045; A61B 1/00172; A61B 50/13;
(Continued)

(56) References Cited

U.S. PATENT DOCUMENTS 6,099,314 A 8/2000 Kopelman et al.
6,334,772 B1 1/2002 Taub et al.
(Continued)

FOREIGN PATENT DOCUMENTS

KR 20230053550 A 4/2023
WO 2023089054 A1 5/2023

OTHER PUBLICATIONS

Anonymous: "How to Share Wi-Fi with an NFC Tag—Seri Tag," Using NFC , Jun. 26, 2023, 20 pages. Retrieved from the Internet: URL:https://web.archive.org/web/2023071308 1735/https://seritag.com/learn/using-nfc/h ow-to-share-wifi-with-nfc-tags, Retrieved on [Oct. 18, 2024], XP093216243.
(Continued)

*Primary Examiner* — Howard D Brown, Jr.
(74) *Attorney, Agent, or Firm* — Lowenstein Sandler LLP

(57) ABSTRACT

An intraoral scanning system comprises an intraoral scanner and a base unit comprising a computing device and a cradle for the intraoral scanner. Responsive to placement of the intraoral scanner into the cradle, the intraoral scanner causes the base unit to wirelessly broadcast a unique identifier according to a first wireless communication protocol and receives the unique identifier. The intraoral scanner uses the unique identifier to establish a wireless connection with the base unit according to a second wireless communication protocol.

26 Claims, 8 Drawing Sheets

(51) Int. Cl.
*A61B 1/24* (2006.01)
*A61B 50/13* (2016.01)
*A61B 90/98* (2016.01)
*A61C 9/00* (2006.01)

(52) U.S. Cl.
CPC .......... *A61B 1/00172* (2013.01); *A61B 50/13* (2016.02); *A61B 90/98* (2016.02); *A61C 9/0053* (2013.01); *A61C 2204/005* (2013.01)

(58) Field of Classification Search
CPC . A61B 90/98; A61B 1/00177; A61B 1/00059; A61C 9/0053; A61C 2204/005
See application file for complete search history.

(56) References Cited

U.S. PATENT DOCUMENTS

| | | | |
|---|---|---|---|
| 6,334,853 B1 | 1/2002 | Kopelman et al. | |
| 6,463,344 B1 | 10/2002 | Pavlovskaia et al. | |
| 6,542,249 B1 | 4/2003 | Kofman et al. | |
| 6,633,789 B1 | 10/2003 | Nikolskiy et al. | |
| 6,664,986 B1 | 12/2003 | Kopelman et al. | |
| 6,697,164 B1 | 2/2004 | Babayoff et al. | |
| 6,845,175 B2 | 1/2005 | Kopelman et al. | |
| 6,979,196 B2 | 12/2005 | Nikolskiy et al. | |
| 7,030,383 B2 | 4/2006 | Babayoff et al. | |
| 7,202,466 B2 | 4/2007 | Babayoff et al. | |
| 7,255,558 B2 | 8/2007 | Babayoff et al. | |
| 7,286,954 B2 | 10/2007 | Kopelman et al. | |
| 7,319,529 B2 | 1/2008 | Babayoff | |
| 7,373,286 B2 | 5/2008 | Nikolskiy et al. | |
| 7,507,088 B2 | 3/2009 | Taub et al. | |
| 7,545,372 B2 | 6/2009 | Kopelman et al. | |
| 7,698,068 B2 | 4/2010 | Babayoff | |
| 7,916,911 B2 | 3/2011 | Kaza et al. | |
| 8,108,189 B2 | 1/2012 | Chelnokov et al. | |
| 8,244,028 B2 | 8/2012 | Kuo et al. | |
| 8,587,582 B2 | 11/2013 | Matov et al. | |
| 8,948,482 B2 | 2/2015 | Levin | |
| D742,518 S | 11/2015 | Barak et al. | |
| 9,192,305 B2 | 11/2015 | Levin | |
| 9,261,356 B2 | 2/2016 | Lampert et al. | |
| 9,261,358 B2 | 2/2016 | Atiya et al. | |
| 9,299,192 B2 | 3/2016 | Kopelman | |
| D760,901 S | 7/2016 | Barak et al. | |
| 9,393,087 B2 | 7/2016 | Moalem | |
| 9,408,679 B2 | 8/2016 | Kopelman | |
| 9,431,887 B2 | 8/2016 | Boltanski | |
| 9,439,568 B2 | 9/2016 | Atiya et al. | |
| 9,451,873 B1 | 9/2016 | Kopelman et al. | |
| D768,861 S | 10/2016 | Barak et al. | |
| D771,817 S | 11/2016 | Barak et al. | |
| 9,491,863 B2 | 11/2016 | Boltanski | |
| D774,193 S | 12/2016 | Makmel et al. | |
| 9,510,757 B2 | 12/2016 | Kopelman et al. | |
| 9,660,418 B2 | 5/2017 | Atiya et al. | |
| 9,668,829 B2 | 6/2017 | Kopelman | |
| 9,675,430 B2 | 6/2017 | Verker et al. | |
| 9,693,839 B2 | 7/2017 | Atiya et al. | |
| 9,717,402 B2 | 8/2017 | Lampert et al. | |
| 9,724,177 B2 | 8/2017 | Levin | |
| 9,844,426 B2 | 12/2017 | Atiya et al. | |
| 10,076,389 B2 | 9/2018 | Wu et al. | |
| 10,098,714 B2 | 10/2018 | Kuo | |
| 10,108,269 B2 | 10/2018 | Sabina et al. | |
| 10,111,581 B2 | 10/2018 | Makmel | |
| 10,111,714 B2 | 10/2018 | Kopelman et al. | |
| 10,123,706 B2 | 11/2018 | Elbaz et al. | |
| 10,136,972 B2 | 11/2018 | Sabina et al. | |
| 10,390,913 B2 | 8/2019 | Sabina et al. | |
| 10,453,269 B2 | 10/2019 | Furst | |
| 10,456,043 B2 | 10/2019 | Atiya et al. | |
| 10,499,793 B2 | 12/2019 | Ozerov et al. | |
| 10,504,386 B2 | 12/2019 | Levin et al. | |
| 10,517,482 B2 | 12/2019 | Sato et al. | |
| 10,708,574 B2 | 7/2020 | Furst et al. | |
| 10,772,506 B2 | 9/2020 | Atiya et al. | |
| 10,888,399 B2 | 1/2021 | Kopelman et al. | |
| 10,952,816 B2 | 3/2021 | Kopelman | |
| 10,980,613 B2 | 4/2021 | Shanjani et al. | |
| D925,739 S | 7/2021 | Shalev et al. | |
| 11,238,586 B2 | 2/2022 | Minchenkov et al. | |
| 11,367,192 B2 | 6/2022 | Kopelman et al. | |
| 11,455,727 B2 | 9/2022 | Minchenkov et al. | |
| 11,478,132 B2 | 10/2022 | Kopelman et al. | |
| 11,563,929 B2 | 1/2023 | Saphier et al. | |
| 11,633,268 B2 | 4/2023 | Moalem et al. | |
| 11,707,238 B2 | 7/2023 | Moshe et al. | |
| RE49,605 E | 8/2023 | Kopelman | |
| 11,759,277 B2 | 9/2023 | Shalev et al. | |
| 11,806,210 B2 | 11/2023 | Moalem | |
| 11,896,461 B2 | 2/2024 | Saphier et al. | |
| 11,937,996 B2 | 3/2024 | Peleg | |
| D1,026,227 S | 5/2024 | Ginzburg et al. | |
| 11,995,839 B2 | 5/2024 | Weiss et al. | |
| 12,033,742 B2 | 7/2024 | Farkash et al. | |
| 12,042,124 B2 | 7/2024 | Rudnitsky et al. | |
| 12,076,200 B2 | 9/2024 | Saphier et al. | |
| 12,127,814 B2 | 10/2024 | Elbaz et al. | |
| 12,144,661 B2 | 11/2024 | Saphier et al. | |
| D1,061,895 S | 2/2025 | Ginzburg et al. | |
| 2018/0263483 A1* | 9/2018 | Elazar | A61B 1/247 |
| 2019/0200903 A1* | 7/2019 | Watson | A61B 5/0013 |
| 2021/0321872 A1 | 10/2021 | Saphier et al. | |
| 2022/0233078 A1 | 7/2022 | Fridman et al. | |
| 2022/0233284 A1* | 7/2022 | Fridman | G16H 50/50 |
| 2022/0323190 A1 | 10/2022 | Kopelman et al. | |
| 2022/0369910 A1 | 11/2022 | Gorfinkel et al. | |
| 2023/0021695 A1 | 1/2023 | Atiya et al. | |
| 2023/0025243 A1 | 1/2023 | Atiya et al. | |
| 2023/0042643 A1 | 2/2023 | Saphier et al. | |
| 2023/0068727 A1 | 3/2023 | Saphier et al. | |
| 2023/0165454 A1* | 6/2023 | Ohtsuka | A61B 1/247 433/29 |
| 2023/0309800 A1 | 10/2023 | Farkash et al. | |
| 2023/0329538 A1* | 10/2023 | Ohtsuka | A61B 1/24 |
| 2023/0346514 A1 | 11/2023 | Coslovsky et al. | |
| 2023/0380942 A1 | 11/2023 | Fain et al. | |
| 2023/0397805 A1* | 12/2023 | Ohtsuka | A61C 19/04 |
| 2023/0414331 A1 | 12/2023 | Saphier | |
| 2024/0024076 A1 | 1/2024 | Fridman | |
| 2024/0033057 A1 | 2/2024 | Saphier et al. | |
| 2024/0036448 A1 | 2/2024 | Atiya et al. | |
| 2024/0115196 A1 | 4/2024 | Moshe et al. | |
| 2024/0122446 A1 | 4/2024 | Fridman et al. | |
| 2024/0156582 A1* | 5/2024 | Kaji | A61C 19/05 |
| 2024/0164624 A1 | 5/2024 | Shalev et al. | |
| 2024/0197448 A1 | 6/2024 | Saphier et al. | |
| 2024/0202921 A1 | 6/2024 | Alkabetz et al. | |
| 2024/0242433 A1* | 7/2024 | Lee | A61B 1/0004 |
| 2024/0245495 A1 | 7/2024 | Moalem et al. | |
| 2024/0285379 A1 | 8/2024 | Saphier et al. | |

OTHER PUBLICATIONS

Anonymous: "Wake-on-LAN," Jul. 5, 2023, 11 pages. Retrieved from the Internet: [URL:https://en.wikipedia.org/w/index.php?title= Wake-on- LAN&oldid=1163591435], Retrieved on [Oct. 18, 2024], XP093216160.

Anonymous: (Wikipedia) "ACPI," Jul. 17, 2023, 09 Pages, Retrieved from the Internet [URL:https://en.wikipedia.org/w/index.php? title= ACPI &oldid= 1165819123], Retrieved on [Oct. 18, 2024], XP093216166.

* cited by examiner

300

400

INTRAORAL SCANNING SYSTEM COMPONENT PAIRING

RELATED APPLICATIONS

This patent application claims the benefit under 35 U.S.C. § 119(e) of U.S. Provisional Application No. 63/514,529, filed Jul. 19, 2023, which is incorporated by reference herein.

TECHNICAL FIELD

Embodiments of the present disclosure relate to the field of dentistry and, in particular, to automatic pairing of two or more components (e.g., intraoral scanners and computing devices) of an intraoral scanning system.

BACKGROUND

Intraoral scanning systems generally include a handheld intraoral scanner and a computing device connected to the handheld intraoral scanner via a wired connection. The wired connection provides power to the intraoral scanner and via the wired connection the computing device receives intraoral scan data from the handheld intraoral scanner. The computing device processes the intraoral scan data and outputs a result of the processing to a display that is either part of the computing device or that is connected to the computing device via a wired connection.

SUMMARY

In a $1^{st}$ aspect of the disclosure, an intraoral scanning system comprises an intraoral scanner and a base unit comprising a computing device and a cradle for the intraoral scanner. Responsive to placement of the intraoral scanner into the cradle, the intraoral scanner causes the base unit to wirelessly broadcast a unique identifier according to a first wireless communication protocol and receives the unique identifier. The intraoral scanner is to use the unique identifier to establish a wireless connection with the base unit according to a second wireless communication protocol.

A $2^{nd}$ aspect of the disclosure may further extend the $1^{st}$ aspect of the disclosure. In the $2^{nd}$ aspect of the disclosure, responsive to the intraoral scanner being powered on, the intraoral scanner establishes the wireless connection with the base unit.

A $3^{rd}$ aspect of the disclosure may further extend the $2^{nd}$ aspect of the disclosure. In the $3^{rd}$ aspect of the disclosure, a component of the intraoral scanner is to remain powered even while the intraoral scanner is turned off, and wherein the component of the intraoral scanner is to store the unique identifier in a memory.

A $4^{th}$ aspect of the disclosure may further extend the $2^{nd}$ or $3^{rd}$ aspect of the disclosure. In the $4^{th}$ aspect of the disclosure, after the intraoral scanner is powered on, the intraoral scanner is configured to: generate a plurality of intraoral scans of a patient's dental arch; and wirelessly transmit the plurality of intraoral scans to the base unit over the wireless connection.

A $5^{th}$ aspect of the disclosure may further extend the $4^{th}$ aspect of the disclosure. In the $5^{th}$ aspect of the disclosure, the base unit is configured to: generate a three-dimensional (3D) surface of at least a portion of the patient's dental arch based on the plurality of intraoral scans; and output the 3D surface to a display of the base unit.

A $6^{th}$ aspect of the disclosure may further extend any of the $1^{st}$ through $5^{th}$ aspects of the disclosure. In the $6^{th}$ aspect of the disclosure, the first wireless communication protocol is a contactless communication protocol, and wherein the second wireless communication protocol is a wireless local area network (WLAN) protocol.

A $7^{th}$ aspect of the disclosure may further extend any of the $1^{st}$ through $6^{th}$ aspects of the disclosure. In the $7^{th}$ aspect of the disclosure, the base unit further comprises a wireless access point that provides a wireless local area network (WLAN) associated with the unique identifier.

An $8^{th}$ aspect of the disclosure may further extend the $7^{th}$ aspect of the disclosure. In the $8^{th}$ aspect of the disclosure, the cradle comprises a contactless communication chip, wherein the computing device is connected to the contactless communication chip via a wired connection through which the computing device is to receive the unique identifier from the contactless communication chip, and wherein the computing device is to set a name of the WLAN to match the unique identifier of the contactless communication chip.

A $9^{th}$ aspect of the disclosure may further extend any of the $1^{st}$ through $8^{th}$ aspects of the disclosure. In the $9^{th}$ aspect of the disclosure, the base unit comprises a wheeled cart.

A $10^{th}$ aspect of the disclosure may further extend any of the $1^{st}$ through $9^{th}$ aspects of the disclosure. In the $10^{th}$ aspect of the disclosure, the cradle comprises a contactless communication chip; and intraoral scanner comprises a contactless communication reader that is to read the unique identifier from the contactless communication chip.

An $11^{th}$ aspect of the disclosure may further extend any of the $1^{st}$ through $10^{th}$ aspects of the disclosure. In the $11^{th}$ aspect of the disclosure, the intraoral scanner is configured to establish the wireless connection with the base unit automatically without user input.

A $12^{th}$ aspect of the disclosure may further extend any of the $1^{st}$ through $11^{th}$ aspects of the disclosure. In the $12^{th}$ aspect of the disclosure, the intraoral scanner comprises a display, and wherein the display is to output a notice while the intraoral scanner is not connected to any base unit.

A $13^{th}$ aspect of the disclosure may further extend any of the $1^{st}$ through $12^{th}$ aspects of the disclosure. In the $13^{th}$ aspect of the disclosure, the base unit comprises a display, and wherein the display is to output a notice while the base unit is not connected to any intraoral scanner.

A $14^{th}$ aspect of the disclosure may further extend any of the $1^{st}$ through $13^{th}$ aspects of the disclosure. In the $14^{th}$ aspect of the disclosure, responsive to a determination by the base unit that it is connected to a plurality of intraoral scanners, the base unit is configured to: send a message to the plurality of intraoral scanners to which the base unit is connected prompting the plurality of intraoral scanners to read a contactless communication chip of the base unit and provide the unique identifier read from the contactless communication chip to the base unit, wherein only an intraoral scanner of the plurality of intraoral scanners currently in the cradle of the base unit successfully reads the unique identifier; receive the unique identifier from the intraoral scanner currently in the cradle of the base unit; and disconnect a remainder of the plurality of intraoral scanners from which the unique identifier was not received.

In a $15^{th}$ aspect of the disclosure, a method comprises: receiving, by an intraoral scanner of an intraoral scanning system, a wireless signal provided by a base unit of the intraoral scanning system, wherein the wireless signal comprises a unique identifier and corresponds to a first wireless communication protocol; and establishing, by the intraoral scanner, a wireless connection with the base unit using the unique identifier, wherein the wireless connection is established according to a second wireless communication protocol.

A 16$^{th}$ aspect of the disclosure may further extend the 15$^{th}$ aspect of the disclosure. In the 16$^{th}$ aspect of the disclosure, the wireless signal is received responsive to placement of the intraoral scanner in a cradle of the base unit.

A 17$^{th}$ aspect of the disclosure may further extend any of the 15$^{th}$ through 16$^{th}$ aspects of the disclosure. In the 17$^{th}$ aspect of the disclosure, the method further comprises: receiving, by the intraoral scanner, a second wireless signal provided by a second base unit, wherein the second wireless signal comprises a second unique identifier and corresponds to the first wireless communication protocol; and establishing, by the intraoral scanner, a new wireless connection with the second base unit using the second unique identifier, wherein the new wireless connection is established according to the second wireless communication protocol.

An 18$^{th}$ aspect of the disclosure may further extend the 17$^{th}$ aspect of the disclosure. In the 18$^{th}$ aspect of the disclosure, the unique identifier corresponds to a first network name of a first wireless local area network (WLAN) provided by the first base unit, and wherein the second unique identifier corresponds to a second network name of a second WLAN provided by the second base unit.

A 19$^{th}$ aspect of the disclosure may further extend any of the 15$^{th}$ through 18$^{th}$ aspects of the disclosure. In the 19$^{th}$ aspect of the disclosure, the wireless signal is received by the intraoral scanner while the intraoral scanner is powered down, and wherein the intraoral scanner establishes the wireless connection with the base unit responsive to the intraoral scanner being powered on.

A 20$^{th}$ aspect of the disclosure may further extend the 19$^{th}$ aspect of the disclosure. In the 20$^{th}$ aspect of the disclosure, a component of the intraoral scanner remains powered even while the intraoral scanner is turned off, the method further comprising: storing the unique identifier by the component of the intraoral scanner.

A 21$^{st}$ aspect of the disclosure may further extend any of the 15$^{th}$ through 20$^{th}$ aspects of the disclosure. In the 21$^{st}$ aspect of the disclosure, the method further comprises: generating a plurality of intraoral scans of a patient's dental arch by the intraoral scanner; and wirelessly transmitting the plurality of intraoral scans to the base unit over the wireless connection, wherein the base unit generates a three-dimensional (3D) surface of at least a portion of the patient's dental arch based on the plurality of intraoral scans and outputs the 3D surface to a display of the base unit.

A 22$^{nd}$ aspect of the disclosure may further extend any of the 15$^{th}$ through 21$^{st}$ aspects of the disclosure. In the 22$^{nd}$ aspect of the disclosure, wherein the first wireless communication protocol is a contactless communication protocol, and wherein the second wireless communication protocol is a wireless local area network (WLAN) protocol.

A 23$^{rd}$ aspect of the disclosure may further extend any of the 15$^{th}$ through 22$^{nd}$ aspects of the disclosure. In the 23$^{rd}$ aspect of the disclosure, the method further comprises: generating an electromagnetic field by a contactless communication reader of the intraoral scanner, wherein the electromagnetic field causes a contactless communication tag of the base unit to output the wireless signal comprising the unique identifier.

A 24$^{th}$ aspect of the disclosure may further extend any of the 15$^{th}$ through 23$^{rd}$ aspects of the disclosure. In the 24$^{th}$ aspect of the disclosure, the base unit comprises a wireless access point that provides a wireless network associated with the unique identifier, and wherein establishing the wireless connection with the base unit comprises: selecting the wireless network having a name corresponding to the unique identifier; and receiving an internet protocol (IP) address from the wireless access point.

A 25$^{th}$ aspect of the disclosure may further extend any of the 15$^{th}$ through 24$^{th}$ aspects of the disclosure. In the 25$^{th}$ aspect of the disclosure, the intraoral scanner establishes the wireless connection with the base unit automatically without user input.

A 26$^{th}$ aspect of the disclosure may further extend any of the 15$^{th}$ through 25$^{th}$ aspects of the disclosure. In the 26$^{th}$ aspect of the disclosure, the method further comprises: outputting a notice indicating that the intraoral scanner is not connected to any base unit to a display of the intraoral scanner until the intraoral scanner is connected to the base unit.

A 26.1$^{th}$ aspect of the disclosure may further extend any of the 15$^{th}$ through 26$^{th}$ aspects of the disclosure. In the 26.1$^{th}$ aspect of the disclosure the intraoral scanner of any of claims 1-12 is configured to perform the method of any of the 15$^{th}$ through 26ths aspects of the disclosure, wherein the intraoral scanner comprises a contactless communication reader to read the unique identifier from a contactless communication tag of the base unit, and wherein the intraoral scanner further comprises a wireless network interface module to receive the unique identifier from the contactless communication reader and use the unique identifier to establish the wireless connection with a wireless access point of the base unit.

In a 27$^{th}$ aspect of the disclosure, a method comprises: reading a contactless communication tag of a base unit of an intraoral scanning system by a computing device of the base unit to determine a unique identifier of the contactless communication tag; configuring an access point of the computing device to cause a wireless local area network (WLAN) associated with the access point to have a name corresponding to the unique identifier; receiving, by the contactless communication tag, a wireless signal from a contactless communication reader of a first intraoral scanner of the intraoral scanning system; broadcasting the unique identifier by the contactless communication tag; receiving a request from the first intraoral scanner to connect to the access point; and establishing a wireless connection between the base unit and the first intraoral scanner.

A 28$^{th}$ aspect of the disclosure may further extend the 27$^{th}$ aspect of the disclosure. In the 28$^{th}$ aspect of the disclosure, the method further comprises: receiving, by the contactless communication tag, a second wireless signal from a second contactless communication reader of a second intraoral scanner; broadcasting the unique identifier by the contactless communication tag; receiving a request from the second intraoral scanner to connect to the access point; and establishing a wireless connection between the base unit and the second intraoral scanner.

A 29$^{th}$ aspect of the disclosure may further extend any of the 27$^{th}$ through 28$^{th}$ aspects of the disclosure. In the 29$^{th}$ aspect of the disclosure, outputting a notice to a display of the base unit indicating that the base unit is not connected to any intraoral scanner until the base unit is connected to the first intraoral scanner.

A 30$^{th}$ aspect of the disclosure may further extend any of the 27$^{th}$ through 29$^{th}$ aspects of the disclosure. In the 30$^{th}$ aspect of the disclosure, the method further comprises: determining that the base unit is wirelessly connected to a plurality of intraoral scanners; sending a message to the plurality of intraoral scanners to which the base unit is connected prompting the plurality of intraoral scanners to read a contactless communication chip of the base unit and provide the unique identifier read from the contactless communication chip to the base unit, wherein only an intraoral scanner of the plurality of intraoral scanners currently in a cradle of the base unit successfully reads the unique identifier; receiving the unique identifier from the intraoral scanner currently in the cradle of the base unit; and disconnecting a remainder of the plurality of intraoral scanners from which the unique identifier was not received.

A 30.1$^{th}$ aspect of the disclosure may further extend any of the 27$^{th}$ through 30$^{th}$ aspects of the disclosure. In the 30.1$^{th}$ aspect of the disclosure, the base unit is configured to perform the method of any of the 27$^{th}$ through 30$^{th}$ aspects of the disclosure, wherein the base unit comprises a cradle comprising the contactless communication tag, the access point, and the computing device, wherein the computing device has a connection to the contactless communication tag and to the access point.

A 30.2$^{th}$ aspect of the disclosure may further extend the 26.1$^{th}$ and the 30.1$^{th}$ aspects of the disclosure. In the 30.2$^{th}$ aspect of the disclosure, an intraoral scanning system comprises the intraoral scanner of the 26.1$^{th}$ aspect of the disclosure and the base unit of the 30.1$^{th}$ aspect of the disclosure.

In a 31$^{st}$ aspect of the disclosure, a wireless intraoral scanner for an intraoral scanning system comprises: a contactless communication reader to read a unique identifier from a contactless communication tag of a base unit of the intraoral scanning system; and a wireless network interface module to receive the unique identifier from the contactless communication reader and use the unique identifier to establish a wireless connection with a wireless access point of the base unit that provides a wireless local area network (WLAN), wherein a name of the WLAN corresponds to the unique identifier.

A 32$^{nd}$ aspect of the disclosure may further extend the 31$^{st}$ aspect of the disclosure. In the 32$^{nd}$ aspect of the disclosure, responsive to the wireless intraoral scanner being powered on, the wireless intraoral scanner establishes the wireless connection with the wireless access point of the base unit.

A 33$^{rd}$ aspect of the disclosure may further extend the 32$^{nd}$ aspect of the disclosure. In the 33$^{rd}$ aspect of the disclosure, the wireless intraoral scanner further comprises: a control unit that remains powered even while the wireless intraoral scanner is turned off, wherein the control unit of the wireless intraoral scanner comprises a memory to store the unique identifier.

A 34$^{th}$ aspect of the disclosure may further extend the 32$^{nd}$ or 33$^{rd}$ aspect of the disclosure. In the 34$^{th}$ aspect of the disclosure, after the wireless intraoral scanner is powered on, the wireless intraoral scanner is configured to: generate a plurality of intraoral scans of a patient's dental arch; and wirelessly transmit the plurality of intraoral scans to the base unit over the wireless connection, wherein the base unit is to generate a three-dimensional (3D) surface of at least a portion of the patient's dental arch based on the plurality of intraoral scans and output the 3D surface to a display of the base unit.

A 35$^{th}$ aspect of the disclosure may further extend any of the 31$^{st}$ through 34$^{th}$ aspects of the disclosure. In the 35$^{th}$ aspect of the disclosure, the contactless communication reader of the wireless intraoral scanner is configured to read the contactless communication tag of the base unit responsive to the wireless intraoral scanner being placed in a cradle of the base unit.

A 36$^{th}$ aspect of the disclosure may further extend any of the 31$^{st}$ through 35$^{th}$ aspects of the disclosure. In the 36$^{th}$ aspect of the disclosure, the wireless intraoral scanner is to establish the wireless connection with the base unit automatically without user input.

A 37$^{th}$ aspect of the disclosure may further extend any of the 31$^{st}$ through 36$^{th}$ aspects of the disclosure. In the 37$^{th}$ aspect of the disclosure, the wireless intraoral scanner comprises a display, and the display is to output a notice while the wireless intraoral scanner is not connected to any base unit.

In a 38$^{th}$ aspect of the disclosure, a base unit for an intraoral scanning system comprises: a cradle comprising a contactless communication tag; a wireless access point; and a computing device having a connection to the contactless communication tag and to the wireless access point; wherein the computing device is configured to: read the contactless communication tag to determine a unique identifier of the contactless communication tag; and configure the wireless access point to cause a wireless local area network (WLAN) associated with the wireless access point to have a name corresponding to the unique identifier; wherein the contactless communication tag is to receive a wireless signal from a contactless communication reader of a first intraoral scanner of the intraoral scanning system and broadcast the unique identifier; and wherein the computing device is to receive a request from the first intraoral scanner to connect to the wireless access point to establish a wireless connection between the base unit and the first intraoral scanner.

A 39$^{th}$ aspect of the disclosure may further extend the 38$^{th}$ aspect of the disclosure. In the 39$^{th}$ aspect of the disclosure, the contactless communication tag is further to receive a second wireless signal from a second contactless communication reader of a second intraoral scanner and subsequently broadcast the unique identifier; and the computing device is further to receive a request from the second intraoral scanner to connect to the wireless access point and to establish a wireless connection between the base unit and the second intraoral scanner.

A 40$^{th}$ aspect of the disclosure may further extend any of the 38$^{th}$ through 39$^{th}$ aspects of the disclosure. In the 40$^{th}$ aspect of the disclosure, the base unit further comprises: a display, wherein the base unit is to output a notice to the display until the base unit is connected to the first intraoral scanner.

A 41$^{st}$ aspect of the disclosure may further extend any of the 38$^{th}$ through 40$^{th}$ aspects of the disclosure. In the 41$^{st}$ aspect of the disclosure, the computing device is further configured to: determine that the base unit is wirelessly connected to a plurality of intraoral scanners; send a message to the plurality of intraoral scanners to which the base unit is connected prompting the plurality of intraoral scanners to read a contactless communication chip of the base unit and provide the unique identifier read from the contactless communication chip to the base unit, wherein only an intraoral scanner of the plurality of intraoral scanners currently in a cradle of the base unit successfully reads the unique identifier; receive the unique identifier from the intraoral scanner currently in the cradle of the base unit; and disconnect a remainder of the plurality of intraoral scanners from which the unique identifier was not received.

A 42$^{nd}$ aspect of the disclosure may further extend any of the 38$^{th}$ through 41$^{st}$ aspects of the disclosure. In the 42$^{nd}$ aspect of the disclosure, the computing device has a wired connection to the contactless communication tag.

BRIEF DESCRIPTION OF THE DRAWINGS

Embodiments of the present disclosure are illustrated by way of example, and not by way of limitation, in the figures of the accompanying drawings.

DETAILED DESCRIPTION

Figure 1:
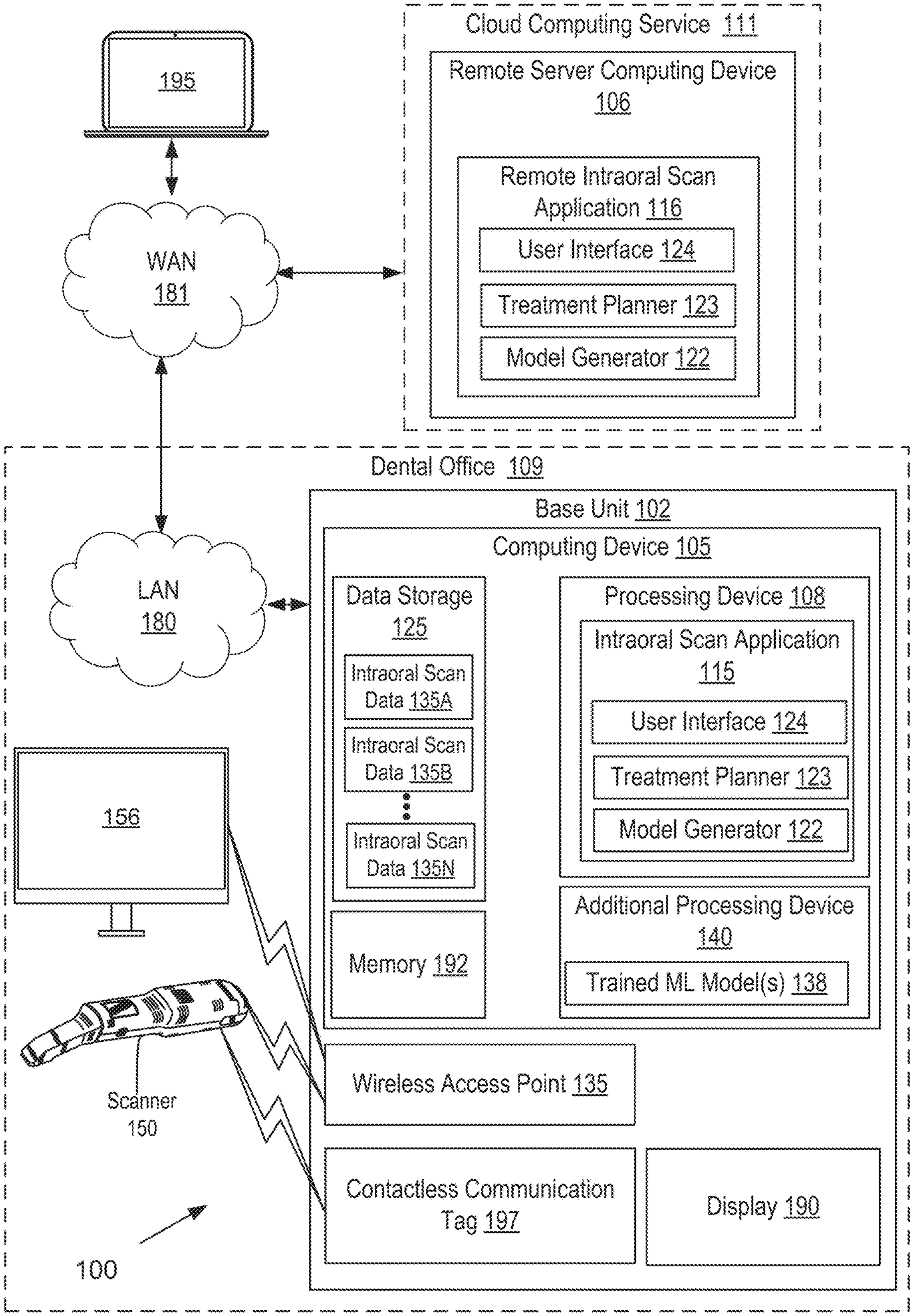
FIG. 1 illustrates an intraoral scanning system, in accordance with embodiments of the present disclosure.

Described herein are embodiments of a wireless intraoral scanning system that includes at least one base station and at least one intraoral scanner. More particularly, embodiments described herein cover automatic pairing (e.g., wireless connecting) of an intraoral scanner and a base unit of an intraoral scanning system. In some instances, a dentist office may include multiple base units and/or multiple intraoral scanners. For example, a dentist office may include a first base unit of an intraoral scanning system in a first room and a second base unit in a second room. The dentist office may additionally include one or more intraoral scanner. The base units may or may not be portable (e.g., may be integrated into a cart in some embodiments). When a doctor is in the first room, they may want the intraoral scanner to communicate with the first base unit, and when the doctor is in the second room, they may want the intraoral scanner to communicate with the second base unit. It can be cumbersome for the doctor to manually connect the intraoral scanner to a desired base unit whenever the intraoral scanner is moved between the first room and the second room. Accordingly, in embodiments an automatic pairing functionality is added to the base unit and the intraoral scanner to enable base units to automatically pair with intraoral scanners without user input.

In one embodiment, each base unit includes a contactless communication tag (also referred to as a contactless communication chip or device) having a unique identifier (ID) and each intraoral scanner includes a contactless communication reader. When an intraoral scanner is brought into close proximity of the contactless communication tag (e.g., placed in a cradle of the first base unit), the contactless communication reader of the intraoral scanner reads the unique ID of the contactless communication tag. The intraoral scanner may additionally include a wireless communication module, which may detect available wireless networks (e.g., wireless local area networks (WLANs)). Each base unit may include an access point that is configured to provide a wireless network having a name that corresponds to the unique ID of the contactless communication tag of that base unit. The intraoral scanner may determine that the available wireless network having the name that corresponds to the unique ID provided by the contactless communication tag corresponds to a wireless network associated with the base unit. The wireless communication module of the intraoral scanner may therefore establish a wireless connection with a wireless access point providing the wireless network having the name corresponding to the unique ID of the contactless communication tag. After such connection is established, the intraoral scanner may send and receive data to/from the base unit. Such data may include, for example, intraoral scans, images, commands to control a user interface of an intraoral scanning application running on the base unit, and so on.

If an intraoral scanner that is paired to (e.g., connected to a wireless network of) a first base unit is brought into close proximity to a second base unit (e.g., placed in a cradle of the second base unit), the above described process is repeated for the second base unit, and the intraoral scanner then pairs with the second base unit. After such pairing of the intraoral scanner with the second base unit, the intraoral scanner may then communicate with the second base unit.

Embodiments simplify the process of connecting intraoral scanners to base units, reducing an amount of time and effort that dentists would otherwise need to spend to establish such connections. Embodiments eliminate a need of a doctor to determine which wireless network is associated with which base unit, navigate through an interface of an intraoral scanner to select a desired wireless network, and/or perform other operations generally performed to connect a device to a wireless network.

FIG. 1 illustrates an intraoral scanning system 100, in accordance with an embodiment. Intraoral scanning system 100 may include only components located at a single location (e.g., at a dentist office 109 or a dental lab) in some embodiments. The intraoral scanning system 100 at a minimum includes a wireless intraoral scanner (also referred to simply as a scanner) 150 and a base unit 102. In some embodiments, the intraoral scanning system 100 may additionally include, or take advantage of, a display 156 and/or a local area network (LAN) 180. Via the LAN 180, the intraoral scanning system 100 (e.g., the computing device 105) may connect to a wide area network (WAN) 181, and through the WAN 181 to a remote server computing device 106. The LAN 180 may include a router, switch, bridge and/or other network device (not shown) that enables communication between multiple devices (e.g., computing device 105 and scanner 150) connected to the LAN 180. The network device may provide wired connections to the LAN using, for example, Ethernet ports, universal serial bus (USB) ports and/or Firewire® ports. The network device may additionally provide wireless connections to the LAN using, for example, a Wi-Fi transceiver.

The WAN 181 may include a public WAN (e.g., the Internet), a private WAN (e.g., an intranet), or a combination thereof. The WAN 181 may include or connect to remote server computing device 106. The server computing device 106 may include a physical machine and/or a virtual machine hosted by a physical machine. The physical machine may be a rackmount server, a desktop computer, or other computing device. In one embodiment, the remote server computing device 106 includes a virtual machine managed and provided by a cloud provider system or cloud computing service 111. Each virtual machine offered by a cloud service provider may be hosted on a physical machine configured as part of a cloud. Such physical machines are often located in a data center. The cloud provider system and cloud may be provided as an infrastructure as a service (IaaS) layer. One example of such a cloud is Amazon's® Elastic Compute Cloud (EC2®).

In some embodiments, computing device 105 connects to scanner 150 wirelessly via a wireless protocol. The connection may be an indirect connection via LAN 180 or may be a direct connection between computing device 105 and scanner 150. For example, scanner 150 may pair with and communicate wirelessly with computing device 105 using a wireless protocol. In embodiments, base unit includes a computing device 105 comprising an access point 135 that provides a wireless network (e.g., a WLAN) that a scanner 150 can connect to in order to pair to the base unit 102.

Base unit 102 may include a computing device 105 having a processing device 108, access point 135, a memory 192, and/or a data storage 125. In some embodiments, memory 192 and data storage 125 are combined. In some embodiments, the processing device 108, access point 135, memory 192 and/or data storage 125 are components of a system on a chip (SoC).

The processing device 108 may be or include a microcontroller, a DSP, a PLC, a microprocessor or programmable logic device such as an FPGA or a CPLD. The processing device 108 may additionally or alternatively include one or more special purpose processor and/or general purpose processor, such as a complex instruction set computing (CISC) microprocessor, reduced instruction set computing (RISC) microprocessor, very long instruction word (VLIW) microprocessor, processor implementing other instruction sets, or processor implementing a combination of instruction sets. Examples of special-purpose processing devices include an application specific integrated circuit (ASIC), a field programmable gate array (FPGA), a digital signal processor (DSP), and network processor. Processing device 108 is configured to execute a intraoral scan application 115 in embodiments.

The memory may include a non-volatile memory (e.g., RAM) and/or a volatile memory (e.g., ROM, Flash, etc.). The data storage 125 may include a local data store and/or a remote data store. The data storage 125 may be or include secondary storage, such as a disc drive, a solid state drive, and so on. Base unit 102 may additionally include a display 190 in embodiments. Computing device 105 may further include one or more additional processing devices 140 in some embodiments.

The access point 135 enables the computing device 105 of base unit 102 to connect to a LAN and/or directly to other devices such as scanner 150. The access point 135 may be configured to manage security, manage sessions, manage communications with external devices, and so forth. In some embodiments, access point 135 provides a WLAN. In one embodiment, the access point 135 is a Wi-Fi® access point that provides a Wi-Fi WLAN. Alternatively, or additionally, the access point 135 may be replaced with a communication module configured to communicate using Bluetooth®, Zigbee®, Internet Protocol version 6 over Low power Wireless Area Networks (6LowPAN), power line communication (PLC), Ethernet (e.g., 10 Megabyte (Mb), 100 Mb and/or 1 Gigabyte (Gb) Ethernet) or other communication protocols.

In some embodiments, computing device 105 includes one or more additional processing device 140. The additional processing device 140 may be a specialized processing device that is optimized for execution of trained machine learning models. Additional processing device 140 may execute one or more trained machine learning (ML) models 138, which may include models for identifying (e.g., on a point, patch or pixel level) moving tissue, foreign objects, excess tissue, soft tissue, hard tissue, and so on. Outputs of the trained machine learning model(s) 138 may be provided to intraoral scan application 115, which may use such outputs to perform one or more actions. Examples of trained machine learning models 138 that may execute on the additional processing device 140 are described in U.S. Pat. No. 11,367,192, issued Jun. 21, 2022, and entitled "Foreign Object Filtering for Intraoral scanning" and U.S. Pat. No. 11,238,586, issued Feb. 1, 2022, and entitled "Excess Material Removal Using Machine learning, which are each incorporated by reference herein in their entirety.

In some embodiments, Based unit 102 is or includes a desktop computing device. In some embodiments, base unit 102 is a laptop or notebook computing device. In some embodiments, base unit is or includes a cart used for intraoral scanning.

In some embodiments, base unit 102 includes a display 190. The display 190 may be an integrated or attached display 190. Base unit 102 may alternatively or additionally be connected to a display 156. Display 190 and display 156 may be, for example, a liquid crystal display (LCD), an organic light emitting diode (OLED) display, a cathode ray tube (CRT) display, or other type of display. Display 156 may be, for example, a television (e.g., smart TV), computer monitor, mobile device that includes a display (e.g., mobile phone, laptop computer, tablet computer, etc.), augmented reality (AR) headset, mixed reality (MR) headset, and so on. Some displays 156 may be physically connected to the computing device 105 via a wired connection. Some displays 156 may be wirelessly connected to computing device 105 via a wireless connection, which may be a direct wireless connection or a wireless connection via a wireless network. For example, display 156 may establish a wireless connection to access point 135. In embodiments, display 156 is a smart display such as a smart television (TV). A smart TV may include an application installed thereon for communicating with and/or acting as a remote display for computing device 105. Alternatively, or additionally, a smart TV may include a web browser, which may be used to navigate to a web page that streams data from computing device 105. For example, the web page may stream a user interface of intraoral scan application 115.

In embodiments, intraoral scanner 150 is a wireless intraoral scanner that includes one or more internal power sources. In one embodiment, intraoral scanner 150 includes a replaceable battery and optionally a secondary power source, such as a secondary rechargeable battery or one or more capacitor. In one embodiment, intraoral scanner includes a wireless power transfer (WPT) receiver and an additional power source (e.g., a rechargeable battery). In some embodiments, the wireless intraoral scanner includes a long distance wireless power transfer (LDWPT) receiver and one or more LDWPT antennas. The LDWPT receiver may receive a wireless power-carrying signal and use the wireless power-carrying signal to power the intraoral scanner under most circumstances. Various power source options for the intraoral scanner 150 are discussed in U.S. application Ser. No. 63/415,942, filed Oct. 13, 2022, and entitled "Power Sources for Wireless Intraoral Scanners," which is incorporated by reference herein in its entirety.

In embodiments, intraoral scanner 150 is wirelessly connected to (e.g., paired to) base unit 102, in particular to computing device 105 of base unit. In one embodiment, scanner 150 is wirelessly connected to computing device 105 via a direct wireless connection. In one embodiment, scanner 150 is wirelessly connected to computing device 105 via a wireless network (e.g., a WLAN). In one embodiment, the wireless network is a Wi-Fi network. In one embodiment, the wireless network is a Bluetooth network, a Zigbee network, or some other wireless network. In one embodiment, the wireless network is a wireless mesh network, examples of which include a Wi-Fi mesh network, a Zigbee mesh network, and so on. In an example, computing device 105 includes a wireless access point (e.g., Wi-Fi access point) 135. Alternatively, base unit 102 may include a wireless access point 135 that is connected to computing device 105 via a wired or wireless connection. Intraoral scanner 150 may include a wireless module such as a Wi-Fi module, and via the wireless module may join the wireless network via the wireless access point 135.

Base unit 102 may include a contactless communication tag 197. Contactless communication tag may be, for example, a near field communication (NFC) tag or a radio frequency identification (RFID) tag in embodiments. The contactless communication tag 197 may be a component of computing device 105, or may be separate from computing device 105 (as shown). In some embodiments, contactless communication tag 197 is integrated into a cradle (not shown) of base unit 102 that may be used to hold scanner 150. The contactless communication tag 197 may have a unique identifier (ID), and may transmit (e.g., broadcast) the unique ID when read by a contactless communication reader (e.g., when a contactless communication reader outputs a magnetic field that causes the contactless communication tag to output the unique ID). Access point 135 may be configured in embodiments to provide a wireless network having a network name that corresponds to the unique ID of the contactless communication tag 197.

Intraoral scanner 150 includes a contactless communication reader (e.g., an NFC reader or an RFID reader). When intraoral scanner 150 is brought within close proximity of contactless communication tag 197 (e.g., anywhere from less than an inch to a few feet from the contactless communication tag), the contactless communication reader may generate a magnetic field that causes the contactless communication tag 197 to output its unique ID. In some embodiments, contactless communication tag 197 is a passive (e.g., unpowered) contactless communication tag. In such embodiments, the electromagnetic field output by the contactless communication reader may provide power to the contactless communication tag. Inductive coupling may be achieved between the contactless communication reader and the contactless communication tag, which may induce a current in the contact less communication tag, causing it to become active and respond to requests from the contactless communication reader or simply output a preconfigured unique ID. In some embodiments, contactless communication tag 197 is an active tag that has its own power source. In some embodiments, passive contactless communication tags 197 provide one-way communication with a contactless communication reader (e.g., in which the contactless communication tag 197 outputs a unique ID but cannot receive data). In some embodiments, active contactless communication tags 197 provide two-way communication.

In one embodiment, contactless communication tag 197 is an NFC tag and the contactless communication reader is an NFC reader. NFC is a short-range wireless communication technology that allows devices to communicate and/or exchange data when they are brought into close proximity, typically within a few centimeters. NFC operates on radio frequency (RF) communication and typically uses a frequency of 13.56 MHz. NFC has a short communication range to ensure that data exchange occurs only when devices are in close proximity, providing a higher level of security compared to other wireless communication technologies like Wi-Fi or Bluetooth.

NFC operates on the principles of electromagnetic induction and radio frequency identification (RFID). NFC technology involves two components: an NFC reader/writer and an NFC tag or device. To perform NFC communication, the NFC reader/writer and the NFC tag or device may be first powered on. In the case of a passive NFC tag, the NFC reader provides power to the NFC tag via inductive coupling. When the NFC-enabled devices are brought within close proximity (usually by touching or placing them near each other, such as by placing the scanner 150 in a cradle comprising an NFC tag), a connection is established between them. When two NFC-enabled devices (e.g., NFC reader and NFC tag) come into close proximity, they use electromagnetic induction to create a link between them. The NFC reader generates an electromagnetic field using its NFC antenna. This field may power the passive NFC tag and enables it to respond. The NFC tag may modulate the electromagnetic field generated by the active device using an NFC antenna of the NFC tag. By changing the load on its NFC antenna, the NFC tag sends back a signal to the NFC reader. This modulation encodes the data to be transmitted. The NFC reader detects the modulated signal from the NFC tag, and decodes the modulated signal to extract the data sent by the NFC tag. In some embodiments, the data sent by the NFC tag is a unique ID of the NFC tag. In some embodiments, the data provided by the NFC tag is used to establish a communication link. Once the communication link is established, the NFC reader and NFC tag may negotiate a communication protocol to be used, which may include a data exchange format and/or a type of interaction mode (e.g., peer-to-peer mode or read/write mode). In read/write mode, the NFC reader can read data from and/or write data to the NFC tag or device. In the peer-to-peer mode, two NFC-enabled devices (e.g., intraoral scanner 150 and base unit 102) can exchange data directly with each other. Once the protocol is agreed upon, data transfer can be performed, which may include the NFC reader reading the unique ID from the NFC tag. Once data exchange is complete or the scanner 150 is moved away from base unit 102, the NFC connection is terminated.

In one embodiment, contactless communication tag 197 is an RFID tag and the contactless communication reader is an RFID reader. RFID operates according to similar principles as NFC. Whereas NFC is designed for short-range communication and operates over very close proximity (e.g., with an effective range of 1-4 inches), RFID encompasses a broader range of communication distances depending on the specific RFID technology being used. RFID can be categorized into three main types based on operating distance, including low-frequency (LF) RFID, high-frequency (HF) RFID, and ultra-high frequency (UHF) RFID. LF RFID operates in the frequency range of 30 kHz to 300 kHz. The typical operating distance is relatively short, ranging from a few centimeters up to about 1 meter (3 feet). HF RFID operates in the frequency range of 3.56 MHz. The typical operating distance is usually within a few centimeters up to about 1 meter (3 feet). UHF RFID operates in the frequency range of 860 MHz to 960 MHZ. UHF RFID can achieve longer communication distances compared to LF and HF RFID. The typical operating range can vary significantly, from a few meters (several feet) up to tens of meters (several tens of feet).

Similar to NFC tags, RFID tags are small electronic devices that include a microchip and an antenna. The microchip stores information or data that uniquely identifies the object associated with the tag. The antenna is responsible for transmitting and receiving radio signals. Similar to NFC readers, RFID readers are devices equipped with antennas that emit radio signals and receive responses from nearby RFID tags. The readers may provide the necessary energy to power the tags during communication. When an RFID reader emits radio signals within its operating frequency range, the signals propagate through the air. If an RFID tag is within the range of the reader, it detects the radio signals. When the RFID tag detects the radio signals, it uses the energy from the incoming signal to power its microchip temporarily. This process is known as "backscatter" or "energy harvesting," where the tag absorbs energy from the reader's signal to activate its circuitry. The powered RFID tag sends a response back to the RFID reader. The response may include the unique identifier or other data stored in the RFID tag's microchip. The RFID tag modulates the reader's signal by altering its impedance or reflecting the signal back to the reader with specific patterns, encoding the data into the response. The RFID reader receives the response from the tag, decodes the data, and interprets it. It can identify the unique identifier and/or other information stored in the tag's memory. The RFID reader can process the received data and perform various actions based on the information obtained from the RFID tag.

Once the scanner 150 determines a unique ID of contactless communication tag 197, scanner 150 may search for an available wireless network (e.g., WLAN) having a name corresponding to the unique ID. This may include scanning for available WLAN access points. In embodiments, scanner 150 listens for beacon frames transmitted by access point 135 to identify its presence and gather information about the wireless network. Upon discovery of the wireless network having the name corresponding to the unique ID, scanner 150 may then attempt to connect to that wireless network. This may include intraoral scanner 150 automatically selecting the wireless network having the name corresponding to the unique ID from a list of available wireless networks.

In some embodiments, access point 135 provides an unsecured wireless network. In some embodiments, access point 135 provides a secured wireless network. In some embodiments, scanner 150 is preconfigured with security information that enables the scanner 150 to authenticate itself to access point 135. For example, scanner 150 may be configured with a password associated with the wireless network. The scanner 150 and access point 135 may then negotiate encryption settings to establish a secure connection. Once the authentication is successful, the scanner 150 may send an association request to the access point 135, which may include a media access control (MAC) address of a wireless module of the intraoral scanner 150 and/or other relevant information. After successful association, the access point 135 may assign an internet protocol (IP) address to the scanner 150 (e.g., using Dynamic Host Configuration Protocol (DHCP)). The IP address allows the scanner 150 to communicate within the WLAN and with computing device 105. With a valid IP address, the scanner 150 is connected to the access point 135, and can send and receive data over the wireless network to/from computing device 105.

Intraoral scanner 150 may be a wireless handheld device that is not tethered to a computer, display, and/or other hardware. The intraoral scanner 150 may be used to perform intraoral scanning of a patient's oral cavity.

Intraoral scanner 150 may include one or more light source, optics and one or more detectors for generating intraoral scan data (e.g., intraoral scans, color images, NIRI images, etc.), one or more buttons and/or touch sensitive inputs (e.g., touch pads and/or touchscreens), and so on. Intraoral scanner 150 may additionally include a memory and/or a processing device (e.g., a controller) for performing initial processing on some or all of the intraoral scan data before it is transmitted to computing device 105. Scanner 150 may additionally include a communication module (e.g., a wireless communication module) such as a network interface controller (NIC) capable of communicating via Wi-Fi, via third generation (3G), fourth generation (4G) and/or fifth generation (5G) telecommunications protocols (e.g., global system for mobile communications (GSM), long term evolution (LTE), Wi-Max, code division multiple access (CDMA), etc.), via Bluetooth, via Zigbee, and/or via other wireless protocols. Alternatively, the scanner 150 may connect to a wide area network (WAN) such as the Internet, and may connect to the computing device 105 and/or remote server computing device 106 via the WAN. Scanner 150 may additionally include a contactless communication reader. One example of a scanner 150 is the iTero® intraoral digital scanner manufactured by Align Technology, Inc. Another example of a scanner 150 is set forth in U.S. Publication No. 2019/0388193, filed Jun. 19, 2019, which is incorporated by reference herein. Two example scanners are described in greater detail below with reference to FIGS. 6-7.

In embodiments, the scanner 150 may include a wireless communication module, a contactless communication reader, one or more rechargeable battery, one or more replaceable battery (which may or may not be rechargeable), a charging module for charging the one or more rechargeable battery and/or a controller (e.g., a processing device) for controlling one or more functions of the scanner 150, among many other components, some of which are discussed herein below.

Intraoral scanner 150 may generate intraoral scans, which may be or include color and/or monochrome 3D information, and send the intraoral scans to computing device 105 via the wireless connection. In some embodiments, intraoral scans include height maps. Intraoral scanner 150 may additionally or alternatively generate color two-dimensional (2D) images (e.g., viewfinder images), and send the color 2D images to computing device 105 via the wireless connection. Scanner 150 may additionally or alternatively generate 2D or 3D images under certain lighting conditions, such as under conditions of infrared or near-infrared (NIRI) light and/or ultraviolet light, and may send such 2D or 3D images to computing device 105 via the wireless connection. Intraoral scans, color images, and images under specified lighting conditions (e.g., NIRI images, infrared images, ultraviolet images, etc.) are collectively referred to as intraoral scan data 135A-N. An operator may start recording scans with the scanner 150 at a first position in the oral cavity, move the scanner 150 within the oral cavity to a second position while the scans are being taken, and then stop recording the scans. In some embodiments, recording may start automatically as the scanner 150 identifies teeth and/or other objects.

An intraoral scan application 115 running on processing device 108 of computing device 105 may wirelessly communicate with the scanner 150 via access point 135 to effectuate an intraoral scan. A result of the intraoral scan may be intraoral scan data 135A, 135B through 135N that may include one or more sets of intraoral scans, one or more sets of viewfinder images (e.g., color 2D images showing a field of view of the intraoral scanner), one or more sets of near-infrared (NIRI) images, and so on. Each intraoral scan may be a two-dimensional (2D) or 3D image that includes a height information (e.g., a height map) of a portion of a dental site, and thus may include x, y and z information. In one embodiment, each intraoral scan is a point cloud. In one embodiment, the intraoral scanner 150 generates numerous discrete (i.e., individual) intraoral scans and/or additional images. In some embodiments, sets of discrete intraoral scans may be merged into a smaller set of blended intraoral scans, where each blended scan is a combination of multiple discrete intraoral scans.

In embodiments, scanner 150 generates and wirelessly sends to computing device 105 a stream of intraoral scan data. The stream of intraoral scan data may include separate streams of intraoral scans, color images and/or NIRI images (and/or other images under specific lighting conditions) in some embodiments. In one embodiment, a stream of blended intraoral scans is sent to computing device 105. In embodiments, the color 2D images in the stream are generated at a first frame rate.

In some embodiments, scanner 150 compresses intraoral scan data (e.g., intraoral scans, color images, NIRI images, etc.) prior to sending the intraoral scan data to computing device 105. In some embodiments, video compression techniques (e.g., optionally based on H.264 codec) are used to compress the stream of intraoral scan data. In some embodiments, intraoral scan data is compressed by a factor of 20 to 40. Accordingly, similarities between sequentially generated scans/images may be used to reduce the amount of data sent for each scan/image. For example, scanner 150 may determine a delta or difference between a previously sent scan and a current scan, and may send over the delta or difference rather than the scan or image. This may significantly reduce an amount of information sent over the wireless connection. Scanner 150 may include an onboard (e.g., internal) processing device that performs compression of at least some of the intraoral scan data.

In some embodiments, scanner 150 does not send whole scans and/or whole images to computing device 105. In one embodiment, scanner 150 may perform one or more computations on the intraoral scan data (e.g., intraoral scans, color images, NIRI images, etc.) to determine one or more areas of interest (AOIs) within the intraoral scan data. The one or more computations may be performed using trained machine learning models that are optimized for resource constrained devices and/or using one or more image processing algorithms. Scanner 150 may then perform data reduction such as by cropping the intraoral scans, images, etc. such that areas outside of the AOIs are cropped out of the scans/images and/or by reducing a resolution of areas outside of the AOIs. Scanner 150 may include an onboard processing device (e.g., a controller or other processing device) that can perform the one or more computations and/or data reduction/cropping of the scan data. The cropped or reduced scans/images are then sent to computing device 105. This, in addition to or instead of performing compression on the intraoral scan data, can reduce a total bandwidth associated with sending intraoral scan data to computing device 105. In one embodiment, AOIs are determined for intraoral scans, and intraoral scans are cropped or reduced before sending to computing device 105, but whole color images such as color viewfinder images are sent to computing device 105 without first cropping or reducing the color images. The uncropped viewfinder image may be presented to a doctor/dentist during the scanning process to show a current field of view of the scanner 150.

Computing device 105 receives intraoral scan data from scanner 150, then stores the intraoral scan data 135A-N in data storage 125. If the intraoral scan data has been compressed, computing device 105 may decompress the intraoral scan data before it is stored. Alternatively, computing device 105 may store the intraoral scan data in a compressed state, and may decompress the intraoral scan data before processing it. In some embodiments, only some of the intraoral scan data is stored (e.g., just the intraoral scans may be stored).

According to an example, a user (e.g., a practitioner) may subject a patient to intraoral scanning. In doing so, the user may apply scanner 150 to one or more patient intraoral locations. The scanning may be divided into one or more segments. As an example, the segments may include a lower dental arch of the patient, an upper dental arch of the patient, one or more preparation teeth of the patient (e.g., teeth of the patient to which a dental device such as a crown or other dental prosthetic will be applied), one or more teeth which are contacts of preparation teeth (e.g., teeth not themselves subject to a dental device but which are located next to one or more such teeth or which interface with one or more such teeth upon mouth closure), and/or patient bite (e.g., scanning performed with closure of the patient's mouth with the scan being directed towards an interface area of the patient's upper and lower teeth). Via such scanner application, the scanner 150 may provide intraoral scan data 135A-N to computing device 105. The intraoral scan data 135A-N may be provided in the form of intraoral scan/image data sets, each of which may include 2D intraoral scans/images and/or 3D intraoral scans/images of particular teeth and/or regions of an intraoral site. In one embodiment, separate scan/image data sets are created for the maxillary arch, for the mandibular arch, for a patient bite, and for each preparation tooth. Alternatively, a single large intraoral scan/image data set is generated (e.g., for a mandibular and/or maxillary arch). Such scans/images may be provided from the scanner to the computing device 105 in the form of one or more points (e.g., one or more pixels and/or groups of pixels). For instance, the scanner 150 may provide such a 3D scan/image as one or more point clouds.

The manner in which the oral cavity of a patient is to be scanned may depend on the procedure to be applied thereto. For example, if an upper or lower denture is to be created, then a full scan of the mandibular or maxillary edentulous arches may be performed. In contrast, if a bridge is to be created, then just a portion of a total arch may be scanned which includes an edentulous region, the neighboring preparation teeth (e.g., abutment teeth) and the opposing arch and dentition. Additionally, the manner in which the oral cavity is to be scanned may depend on a doctor's scanning preferences and/or patient conditions.

By way of non-limiting example, dental procedures may be broadly divided into prosthodontic (restorative) and orthodontic procedures, and then further subdivided into specific forms of these procedures. Additionally, dental procedures may include identification and treatment of gum disease, sleep apnea, and intraoral conditions. The term prosthodontic procedure refers, inter alia, to any procedure involving the oral cavity and directed to the design, manufacture or installation of a dental prosthesis at a dental site within the oral cavity (intraoral site), or a real or virtual model thereof, or directed to the design and preparation of the intraoral site to receive such a prosthesis. A prosthesis may include any restoration such as crowns, veneers, inlays, onlays, implants and bridges, for example, and any other artificial partial or complete denture. The term orthodontic procedure refers, inter alia, to any procedure involving the oral cavity and directed to the design, manufacture or installation of orthodontic elements at a intraoral site within the oral cavity, or a real or virtual model thereof, or directed to the design and preparation of the intraoral site to receive such orthodontic elements. These elements may be appliances including but not limited to brackets and wires, retainers, clear aligners, or functional appliances.

During an intraoral scan session, intraoral scan application 115 receives and processes intraoral scan data (e.g., intraoral scans) and generates a 3D surface of a scanned region of an oral cavity (e.g., of a dental site) based on such processing. To generate the 3D surface, intraoral scan application 115 may register and "stitch" or merge together the intraoral scans generated from the intraoral scan session in real time or near-real time as the scanning is performed. In one embodiment, performing registration includes capturing 3D data of various points of a surface in multiple scans (views from a camera), and registering the scans by computing transformations between the scans. The 3D data may be projected into a 3D space for the transformations and stitching. The scans may be integrated into a common reference frame by applying appropriate transformations to points of each registered scan and projecting each scan into the 3D space.

In one embodiment, registration is performed for adjacent or overlapping intraoral scans (e.g., each successive frame of an intraoral video). In one embodiment, registration is performed using blended scans and/or reduced or cropped scans. Registration algorithms are carried out to register two or more adjacent intraoral scans and/or to register an intraoral scan with an already generated 3D surface, which essentially involves determination of the transformations which align one scan with the other scan and/or with the 3D surface. Registration may involve identifying multiple points in each scan (e.g., point clouds) of an scan pair (or of a scan and the 3D model), surface fitting to the points, and using local searches around points to match points of the two scan (or of the scan and the 3D surface). For example, intraoral scan application 115 may match points of one scan with the closest points interpolated on the surface of another image, and iteratively minimize the distance between matched points. Other registration techniques may also be used. Intraoral scan application 115 may repeat registration and stitching for all scans of a sequence of intraoral scans and update the 3D surface as the scans are received.

In one embodiment, the scanner 150 is used as an input device to control the view of the 3D surface of a dental site. Embodiments of the present invention enable a user to perform operations (such as to control or navigate a user interface of intraoral scan application 115 and/or to manipulate medical images or a representation generated from medical images) while still engaged with a patient. Scanner 150 may include one or more buttons, one or more touch sensitive inputs (e.g., touch pads and/or touchscreens) and/or an inertial measurement unit (IMU) including one or more inertial measurement devices (e.g., accelerometers and/or gyroscopes) that may be used to navigate the user interface of the intraoral scan application 115 and/or manipulate a generated 3D surface.

A user (e.g., a practitioner) may navigate through scanning segments (e.g., an upper dental arch segment, a lower dental arch segment, a bite segment, and optionally a separate segment for each preparation tooth) via a user interface (UI) of the intraoral scan application 115 by various input devices, such as a cursor control device (e.g., a mouse), a remote control (e.g., of a smart TV), a touch input device (e.g., touchscreen) of a scanner 150, etc. In embodiments, a scanner 150 may allow the user to easily navigate or control the user interface of the intraoral scan application 115 using the touch input and/or buttons of the scanner 150. For example, the user may utilize a combination of buttons and various touch gestures on the touch sensor of the scanner 150 to navigate the intraoral scan application 115. In some embodiments, intraoral scanner 150 includes a touchscreen that outputs one or more virtual buttons. A user may interact with the one or more virtual buttons (e.g., by pressing a virtual button) to send a control signal to the intraoral scan application 115. Which virtual buttons are displayed on the intraoral scanner's 150 touchscreen may depend on a current mode of the intraoral scan application 115.

Navigation or control of the user interface of the intraoral scan application 115 may be performed via user input. The user input may be performed through various devices, such as a touch input device (e.g., a touchscreen), keyboard, mouse, or other similar control devices of one or more device wirelessly connected to computing device 105. User input may also be provided via scanner 150 in embodiments, such as via a touchpad and/or touchscreen of the intraoral scanner 150. Navigation of the user interface may involve, for example, navigating between various modules or modes, navigating between various segments, controlling the viewing of the 3D rendering, or any other user interface navigation. A touch sensitive scanner (e.g., which may include a touchscreen) allows the user to navigate or control the user interface without continuously disengaging from the patient.

In one embodiment, intraoral scan application 115 includes a touch input module (not shown) that receives and interprets touch input data from scanner 150. Scanner 150 may receive different types of touch input such as hold gestures, swipe gestures, tap gestures, circular gestures, and so on. Additionally, or alternatively, a touchscreen of the intraoral scanner 150 may display multiple different virtual buttons, and user interaction with each of the virtual buttons may trigger a different action in intraoral scan application 115. The touch input module may determine a type of touch gesture that a user performed based on the received touch input and/or what virtual button was pressed based on a detected finger. The touch input module may then initiate functions or operations of the user interface (or intraoral scan application generally) responsive to the determined touch gesture. The functions or operations that are initiated may depend both on the current mode of the intraoral scan application 115 and the determined touch gesture and/or pressed virtual button. Accordingly, the same touch gesture or finger interaction with a same region of the touchscreen may cause a first function to be performed in a first mode of the intraoral scan application and may cause a second function to be performed in a second mode. Specific modes of operation and touch gestures and/or virtual buttons that initiate operations or functions for those modes are discussed in greater detail below.

In one embodiment, computing device 105 executing intraoral scan application 115 receives a touch input from a touch sensor (e.g., a touchpad or touchscreen) of scanner 150 (e.g., which may include a press of a virtual button on a touchscreen) and/or a button press from a button of scanner 150 during an intraoral scan session. In one embodiment, intraoral scan application 115 determines whether the touch input is a hold gesture or a swipe gesture. The computing device may then perform a first function or operation to control a user interface of the intraoral scan application if the touch input is a hold gesture (or a particular button of virtual button is depressed) and a second function or operation to control the user interface of the intraoral scan application if the touch input is a swipe gesture (or another button or virtual button is depressed). Examples of functions that may be performed include activating a gyroscope in the intraoral scanner 150, using data from the gyroscope to control an orientation of a virtual 3D surface (e.g., if a hold gesture is detected) and proceeding to next or previous scan segments (e.g., if a swipe gesture is detected). The functions or operations performed responsive to the hold or swipe gestures and/or responsive to a user pressing a virtual button of a touchscreen on the intraoral scanner 150 may be functions that traditionally are performed responsive to a user using a keyboard, mouse and/or touchscreen of a computer. Results of the inputs from the scanner 150 (e.g., button pushes, virtual button pushes, swipe gestures, hold gestures, movement of the scanner 150, etc.) may cause one or more menus or options of the intraoral scan application 115 to be navigated or transitioned between, and/or an updated menu or options to be output to a display 156, 190 associated with the intraoral scanner 150 and/or to a touchscreen of the intraoral scanner 150. In some embodiments, pressing a particular button or buttons (including one or more virtual buttons of a touchscreen) or performing a hold gesture of a touch sensitive input causes intraoral scan application 115 to output a navigation overlay to a display 156, 190. While and/or after the button(s) and/or virtual buttons are pushed and/or during the hold gesture of the touch sensitive input, a user may move the scanner 150 and motion of the scanner may be used as an input to navigate the navigation overlay. For example, the scanner 150 may be moved left to select a first menu option (e.g., switch to previous scan segment), right to select a second menu option (e.g., switch to next scan segment), up to select a third menu option or down to select a fourth menu option. The movement of the scanner may register as an input that causes a user interface of the intraoral scan application 115 to be updated, and the updated user interface may be output to the display 156, 190 associated with scanner 150.

By providing touch sensors, touchscreens and/or buttons in the intraoral scanner 150 and an intraoral scan application 115 that can respond to touch input from such touch sensors, that can respond to input from touchscreens (e.g., presses of virtual buttons displayed on a touchscreen) and/or that can respond to use of the buttons, embodiments improve the efficiency of performing intraoral scans. Additionally, display 156 may not include an input device for controlling intraoral scan application 115. However, scanner 150 may function as such an input device for controlling intraoral scan application 115. For example, if the intraoral scan application 115 is outputting image data to display 156, then a user of scanner 150 may press a physical button, press a virtual button of a touchscreen on the intraoral scanner 150 and/or use a hold gesture on a touch input of the scanner 150 to activate a view mode. During the view mode, the user may move the scanner and/or interface with the touchscreen or touch pad on the intraoral scanner 150 to rotate a view of a 3D surface or 3D model of a dental site. The user may release the button, virtual button or hold gesture to resume a scanning mode and continue generating intraoral scans. Alternatively, the user may press a different virtual button to resume the scanning mode and continue generating intraoral scans.

When a scan session is complete (e.g., all scans for an intraoral site or dental site have been captured), intraoral scan application 115 may send the intraoral scan data (e.g., including at a minimum intraoral scans) to remote server computing device 106 for processing by remote intraoral scan application 116. Remote intraoral scan application 116 may include a model generator 122 that may process the intraoral scan data to generate one or more virtual 3D model of a patient's dental arch or dental arches. Additionally, or alternatively, intraoral scan application may include model generator 122. Model generator 122 may generate a virtual 3D model (also referred to as a digital 3D model) of one or more scanned dental sites. The virtual 3D model includes a 3D surface of the one more scanned dental sites. To generate the virtual 3D model, model generator 122 may register and "stitch" or merge together the intraoral scans generated from the intraoral scan session. In one embodiment, registration is performed for adjacent and/or overlapping intraoral scans (e.g., each successive frame of an intraoral video). In one embodiment, registration is performed using blended scans and/or reduced or cropped scans. Registration algorithms may be carried out to register two or more adjacent intraoral scans and/or to register an intraoral scan with a 3D model, which essentially involves determination of the transformations which align one scan with the other scan and/or with the 3D model. Registration may involve identifying multiple points in each scan (e.g., point clouds) of a scan pair (or of a scan and the 3D model), surface fitting to the points, and using local searches around points to match points of the two scans (or of the scan and the 3D model). For example, model generator 122 may match points of one scan with the closest points interpolated on the surface of another scan, and iteratively minimize the distance between matched points. Other registration techniques may also be used. The registration and stitching that are performed to generate the 3D model may be more accurate than the registration and stitching that are performed to generate the 3D surface that is shown in real time or near-real time during the scanning process.

Model generator 122 may repeat registration for all scans of a sequence of intraoral scans to obtain transformations for each scan, to register each scan with the previous one and/or with a common reference frame (e.g., with the 3D model). Model generator 122 may integrate all scans (or all scans associated with a segment) into a single virtual 3D model by applying the appropriate determined transformations to each of the scans. Each transformation may include rotations about one to three axes and translations within one to three planes. In some embodiments, a first model of an upper dental arch and a second model of a lower dental arch are generated.

In some embodiments, intraoral scan application 115 includes a local version of model generator 122, which can generate virtual 3D models of dental arches locally on computing device 105.

A user (e.g., a dentist) may access and view the virtual 3D model(s) by accessing a user interface 124 of remote intraoral scan application 116 from a client computing device 195. Alternatively, a user may access and view the virtual 3D models by interfacing with computing device 105. The client computing device 195 may be any computing device, such as a tablet computer, a desktop computer, a mobile phone, a laptop, a notebook computer, and so on.

User interface 124 of remote intraoral scan application 116 or of intraoral scan application 115 may generate a view of the 3D model and output the view to client computing device 195 for display of the 3D model to a user (e.g., a doctor) via a display of the client computing device 195. A doctor may then interface with the client computing device 195 or computing device 105 to generate commands to change the view of the 3D model (e.g., by zooming in or out, panning, rotating, etc.). The client computing device 195 may send the command to remote intraoral scan application 116, which may change the view of the 3D model, and then send the updated view to the client computing device 195. Alternatively, a user may provide commands to computing device 105 for changing a view of a 3D model. In this manner, the 3D model can be checked visually by the doctor. The doctor can virtually manipulate the 3D model via the user interface of the client computing device 195 or computing device 105 with respect to up to six degrees of freedom (i.e., translated and/or rotated with respect to one or more of three mutually orthogonal axes) using suitable user controls (hardware and/or virtual) to enable viewing of the 3D model from any desired direction. The doctor may review (e.g., visually inspect) the generated 3D model of an intraoral site and determine whether the 3D model is acceptable (e.g., whether a margin line of a preparation tooth is accurately represented in the 3D model).

In one embodiment, remote intraoral scan application 116 and/or intraoral scan application 115 includes a treatment planner 123 configured to perform treatment planning for orthodontic treatment and/or prosthodontic treatment. In some embodiments, processing device 108 includes a local version of treatment planner 123 and/or user interface 124. Treatment planner 123 may additionally perform dental diagnostics and/or prognostics. Via the user interface 124, a practitioner may view one or more of the upper dental arch, the lower dental arch, a particular preparation tooth and/or the patient bite, each of which may be considered a separate scan segment or mode. The treatment planner 123 in embodiments generates an orthodontic treatment plan, including a 3D model for a final tooth arrangement and 3D models for one or more intermediate tooth arrangements. Treatment planner 123 may additionally or alternatively perform diagnostics of a patient's oral cavity and/or provide a prognosis of one or more dental conditions and/or suggested treatments for the one or more dental conditions. The treatment planner 123 may further perform one or multiple different analyses of the patient's dental arches and/or bite. The analyses may include an analysis for identifying tooth cracks, an analysis for identifying gum recession, an analysis for identifying tooth wear, an analysis of the patient's occlusal contacts, an analysis for identifying crowding of teeth (and/or spacing of teeth) and/or other malocclusions, an analysis for identifying plaque, an analysis for identifying tooth stains, an analysis for identifying caries, and/or other analyses of the patient's dentition. Once the analyses are complete, a dental diagnostics summary and/or detailed dental diagnostics information optionally including prognosis and/or treatment options may be presented to a client computing device 195 and/or via display 156, 190. A doctor may control the treatment planner 123 and navigate menus and options of the treatment planner using the client computing device 195, computing device 105 and/or scanner 150.

Once an adequate set of 3D models is generated, the 3D models may be saved to the patient profile. The dental practitioner may then navigate to a delivery mode to electronically send the completed patient profile to a processing center. The processing center may then generate the custom made series of clear aligners for the patient and deliver the clear aligners to the dental practitioner. The patient would then return to the dental practitioner to receive the first set of clear aligners and verify the clear aligners properly fit onto the patient's teeth.

Figure 2A:
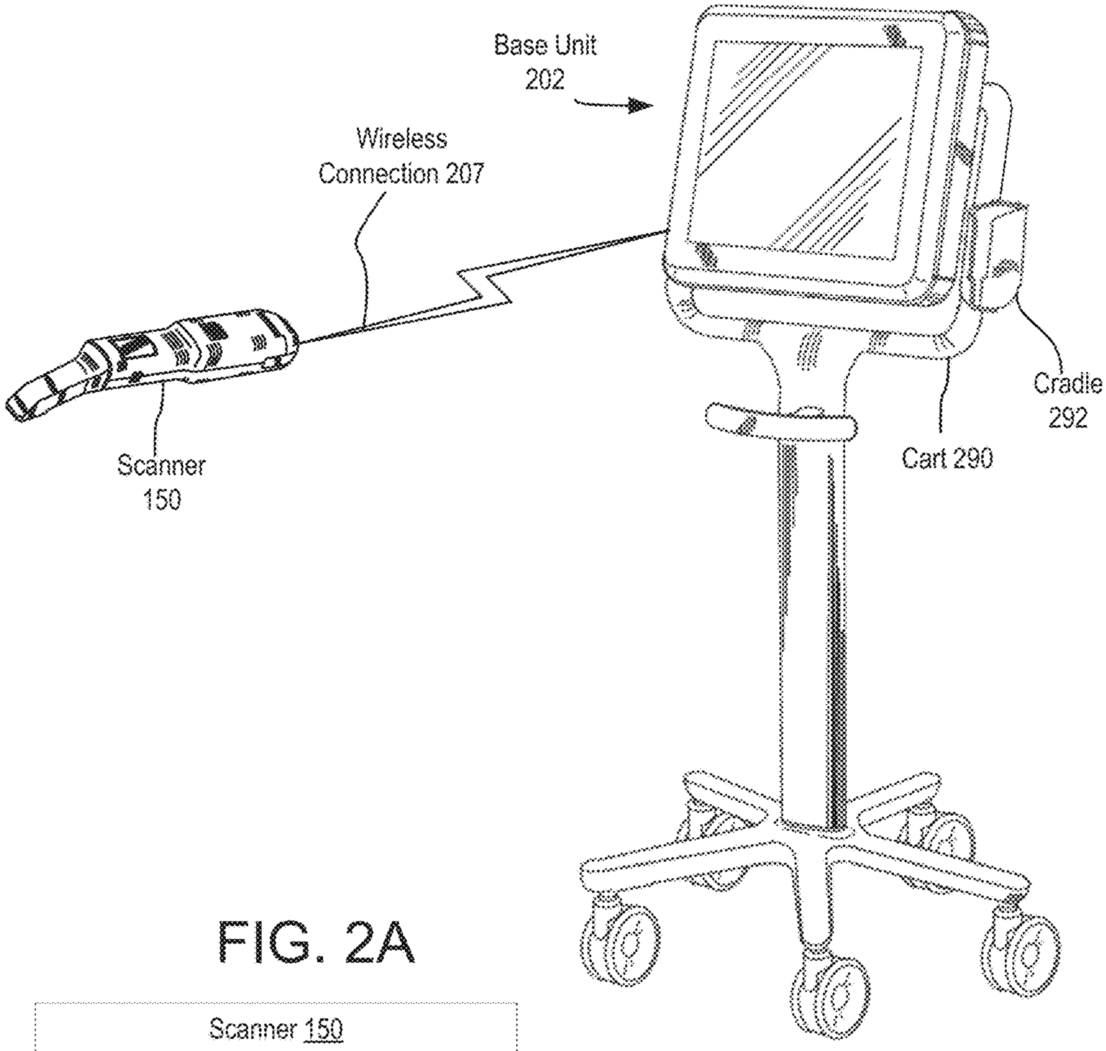
FIGS. 2A-B illustrate pairing of an intraoral scanner with a base unit, in accordance with embodiments of the present disclosure.
Figure 2B:
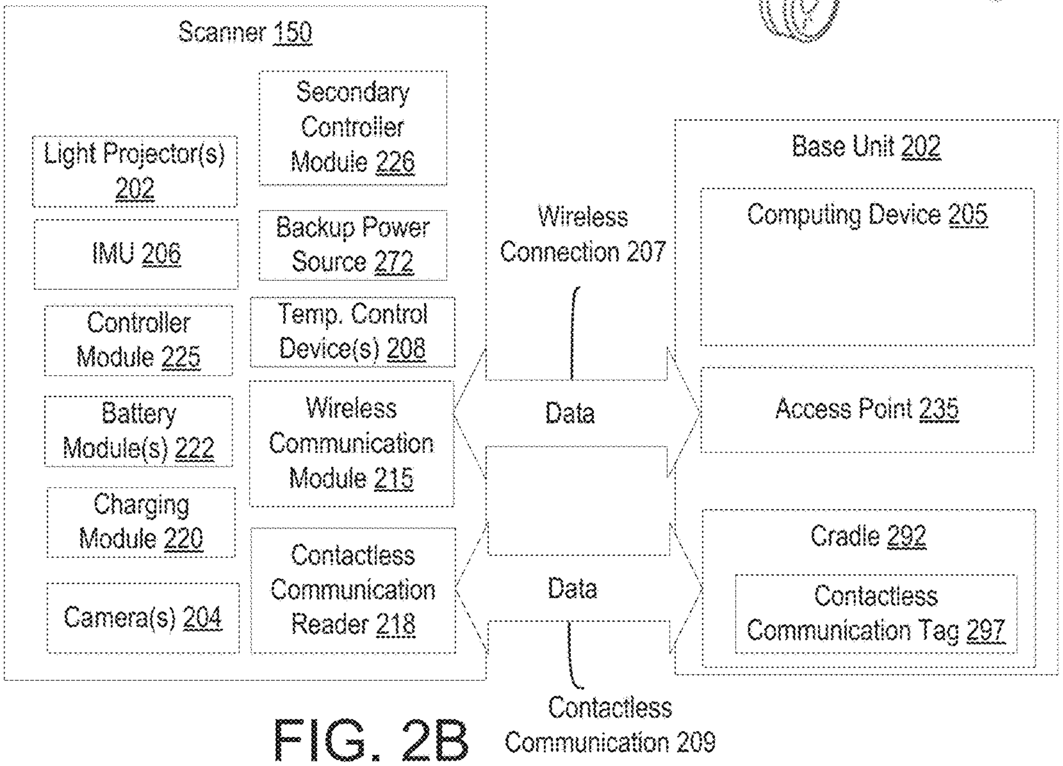

FIGS. 2A-B illustrate pairing of an intraoral scanner with a base unit, in accordance with embodiments of the present disclosure. Scanner 150 in one embodiment includes one or more light projectors 202, one or more cameras 204 (e.g., image capture devices such as charge coupled devices (CCDs) and/or complementary metal-oxide-semiconductor (CMOS) devices), an inertial measurement unit (IMU) 206, one or more temperature control devices 208 (e.g., heaters, fans, coolant systems, etc.), actuators (not shown), a contactless communication reader 218, and/or other components such as those discussed with reference to FIGS. 6-7. In embodiments, the IMU 206 may include one or more accelerometers, gyroscopes, micro-electro-mechanical systems (MEMS) devices for measuring motion and/or inertia, and so on. Scanner 150 may additionally or alternatively include a controller module 225, a secondary controller module 226, one or more battery modules 222 (e.g., a replaceable battery module and/or an integrated rechargeable battery module), a charging module 220, a wireless communication module 215 and/or a backup power source 272.

Wireless communication module 215 may include a network interface controller (NIC) capable of communicating via Wi-Fi, via third generation (3G), fourth generation (4G) and/or fifth generation (5G) telecommunications protocols (e.g., global system for mobile communications (GSM), long term evolution (LTE), Wi-Max, code division multiple access (CDMA), etc.), via Bluetooth, via Zigbee, and/or via other wireless protocols. Contactless communication reader 218 may be any type of contactless communication reader, such as an RFID reader or an NFC reader.

Battery modules 222 may include an integrated rechargeable battery module that may include one or more removable and/or replaceable rechargeable battery. The rechargeable battery may include a lithium-ion battery, for example. Battery modules 222 may additionally or alternatively include a replaceable battery module that can receive non-rechargeable batteries. Accordingly, battery modules 222 may include just one or more rechargeable batteries, just one or more replaceable batteries, or both one or more rechargeable batteries and one or more replaceable batteries.

In some embodiments, scanner 150 includes a backup power source 272. Backup power source 272 may be a non-replaceable power source, and may sustain many (e.g., thousands of) charging/discharging cycles. In one embodiment, backup power source 272 is a rechargeable battery, such as a lithium-ion battery. In one embodiment, backup power source 272 comprises one or more capacitors, such as a bank of capacitors. In one embodiment, backup power source 272 includes one or more super-capacitors. In embodiments, backup power source 272 is configured to provide up to about 1 W (e.g., up to 1 W) of power for at least about 45 seconds (e.g., for at least 45 seconds, for at least 60 seconds, etc.). In one embodiment, backup power source 272 contains 2-4 (e.g., 3) capacitors each having 5 mWh of stored energy. Accordingly, in embodiments backup power source 272 can provide 1 W of power consumption with a 1 V cutoff voltage for a threshold period of time. In some embodiments, backup power source comprises a wireless power transfer (WPT) receiver.

Charging module 220 may include a charger for charging a rechargeable battery in a battery module 222. The charging module 220 may include a traditional charger that receives a current via a wired connection. The charging module 220 may additionally or alternatively include an inductive or wireless charger component that includes a secondary coil configured to inductively couple with a primary coil of an external wireless charger that is external to the scanner 150 (e.g., that is integrated into a cradle for the scanner 150).

Controller module 225 may include a processing device, memory, and/or other components for controlling one or more operations of scanner 150. In one embodiment, controller module 225 includes a system on a chip (SoC) including a processor and memory. In one embodiment, controller module 225 includes firmware and/or software installed thereon that controls a functionality of scanner 150. The processing device of controller module 225 may be or include a microcontroller, a DSP, a PLC, a microprocessor or programmable logic device such as an FPGA or a CPLD. The processing device may additionally or alternatively include one or more special purpose processor and/or general purpose processor, such as a complex instruction set computing (CISC) microprocessor, reduced instruction set computing (RISC) microprocessor, very long instruction word (VLIW) microprocessor, processor implementing other instruction sets, or processor implementing a combination of instruction sets. Examples of special-purpose processing devices include an application specific integrated circuit (ASIC), a field programmable gate array (FPGA), a digital signal processor (DSP), and network processor.

The memory of controller module 225 may include a non-volatile memory (e.g., RAM) and/or a volatile memory (e.g., ROM, Flash, etc.).

In some embodiments, scanner 150 includes a secondary controller module 226. Secondary controller module 226 may include one or more low power components, which may include a processing device, a memory, and so on. In one embodiment, secondary controller module 226 includes an SoC. Secondary controller module 226 may remain powered even when the scanner 150 is turned off. In some embodiments, secondary controller module 226 determines when to provide power to contactless communication reader 218, and provides power to contactless communication reader 218 even while scanner 150 is turned off in order to enable scanner 150 to obtain information usable to pair with base unit 202. Contactless communication reader 218 may obtain a unique ID from a contactless communication tag 297 of base unit 202 while scanner 150 is turned off, and may store the unique ID in a memory. Once scanner 150 is turned on, controller module 225, secondary controller module 226 and/or wireless communication module 215 may retrieve the unique ID from memory and may determine which wireless network to connect to based on the unique ID. In some embodiments, secondary controller module 226 causes the wireless communication module 226 to be powered while the intraoral scanner 150 is turned off, enabling a wireless connection to be established between the intraoral scanner and the base unit 202 while the intraoral scanner is turned off.

Scanner 150 and base unit 202 together make up an intraoral scanning system (or a part of an intraoral scanning system), and may wirelessly connect or pair to form the intraoral scanning system. In embodiments, both scanner 150 and base unit 202 are capable of communicating using at least two wireless communication protocols. In embodiments, scanner 150 and base unit 202 use a first wireless communication protocol (e.g., NFC or RFID) to communicate a unique ID to scanner 150 and use a second wireless communication protocol (e.g., a WLAN protocol such as Wi-Fi) to establish a wireless connection based on the unique ID communicated using the first wireless communication protocol. As shown, base unit 202 may include a computing device 205, a wireless access point 235, a cradle 292, and a contactless communication tag 297. In one embodiment, access point 235 is a component of computing device 205. In one embodiment, access point 235 is a component of cradle 292. Alternatively, the access point 235 may not be a component of computing device 205 or cradle (e.g., may be separate from computing device 205). In one embodiment, contactless communication tag 297 be a component of cradle 292 (as shown). In one embodiment, contactless communication tag 297 may not be a component of cradle 292 (e.g., may be separate from cradle 292).

When scanner 150 is brought within close proximity to contactless communication tag 297 (e.g., is placed in cradle 292), contactless communication reader 218 performs contactless communication 209 with base unit 202, which may include reading the unique ID of contactless communication tag 297. Wireless communication module 215 may then connect to the wireless network provided by access point 235 that has a name corresponding to the unique ID. Once a wireless connection 207 (e.g., via a WLAN) is established between base unit 202 and scanner 150, scanner 150 may exchange data with computing device 205 via the wireless connection 207. As shown, scanner 150 is not physically connected (e.g., via a cable) to any computing device or power supply. Accordingly, scanner 150 may operate in a fully wireless mode of operation, and may draw on power from onboard batteries of battery module 222 and/or on backup power source 272, and exchanges data with computing device 105 via wireless connection 207. Alternatively, scanner 150 may include a power cord which may plug into base unit 202 and/or a power outlet.

In embodiments, base unit 202 includes a cart 290 on which is mounted computing device 105 (e.g., which may include a touchscreen display). Base unit 202 may include an onboard medical grade power adapter (not shown), and may include a charger 292 for charging scanner 150 and/or a battery pack (e.g., housing one or more replaceable batteries) that can be removed from scanner 150. Base unit 202 may further include an onboard cradle for holding the scanner 150 when scanner 150 is not in use. In some embodiments, cradle 292 is also a charger for scanner 150.

Figure 3:
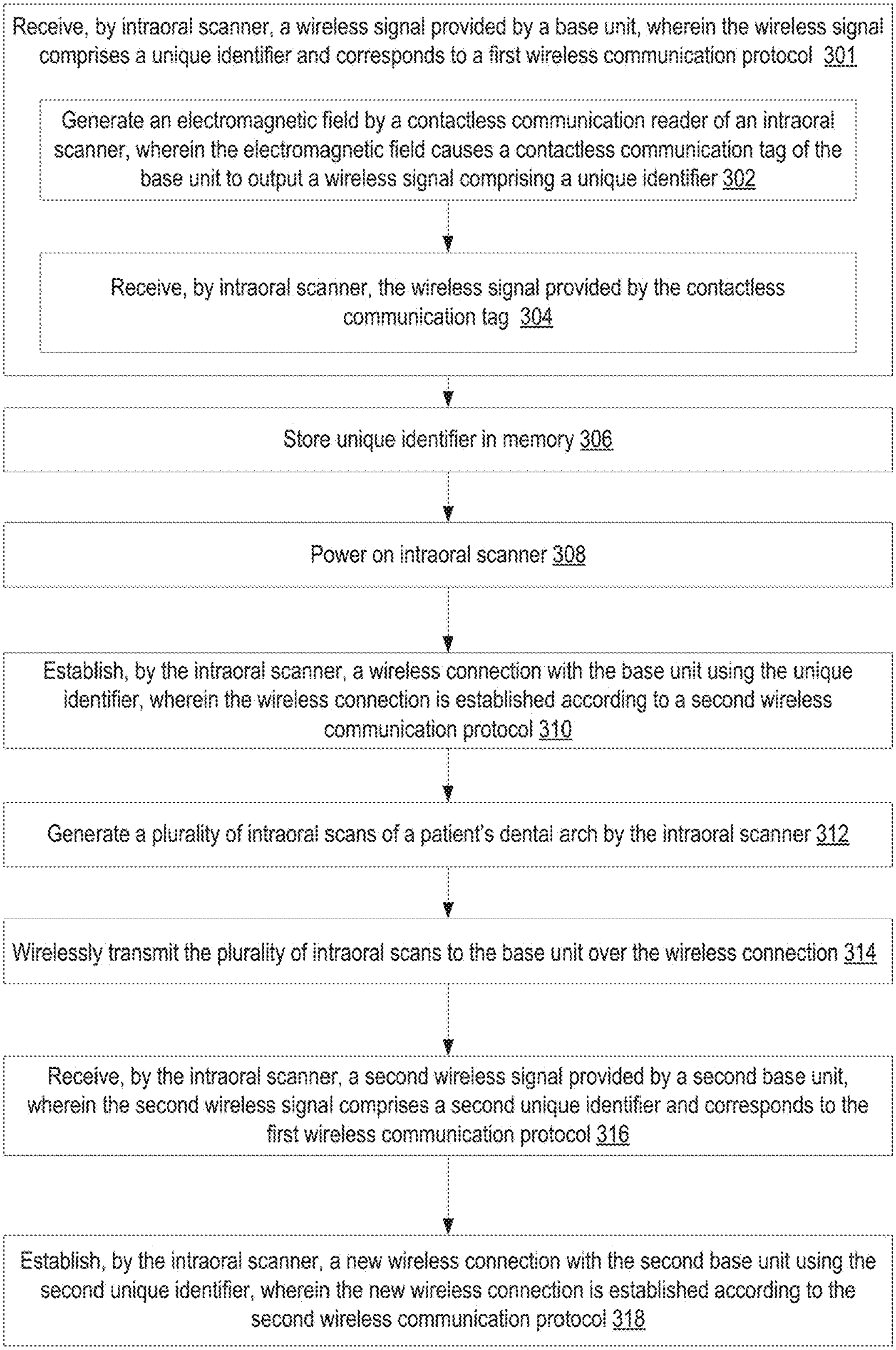
FIG. 3 illustrates a flow diagram for a method performed by an intraoral scanner to pair with a base unit of an intraoral scanning system, in accordance with embodiments of the present disclosure.
Figure 4:
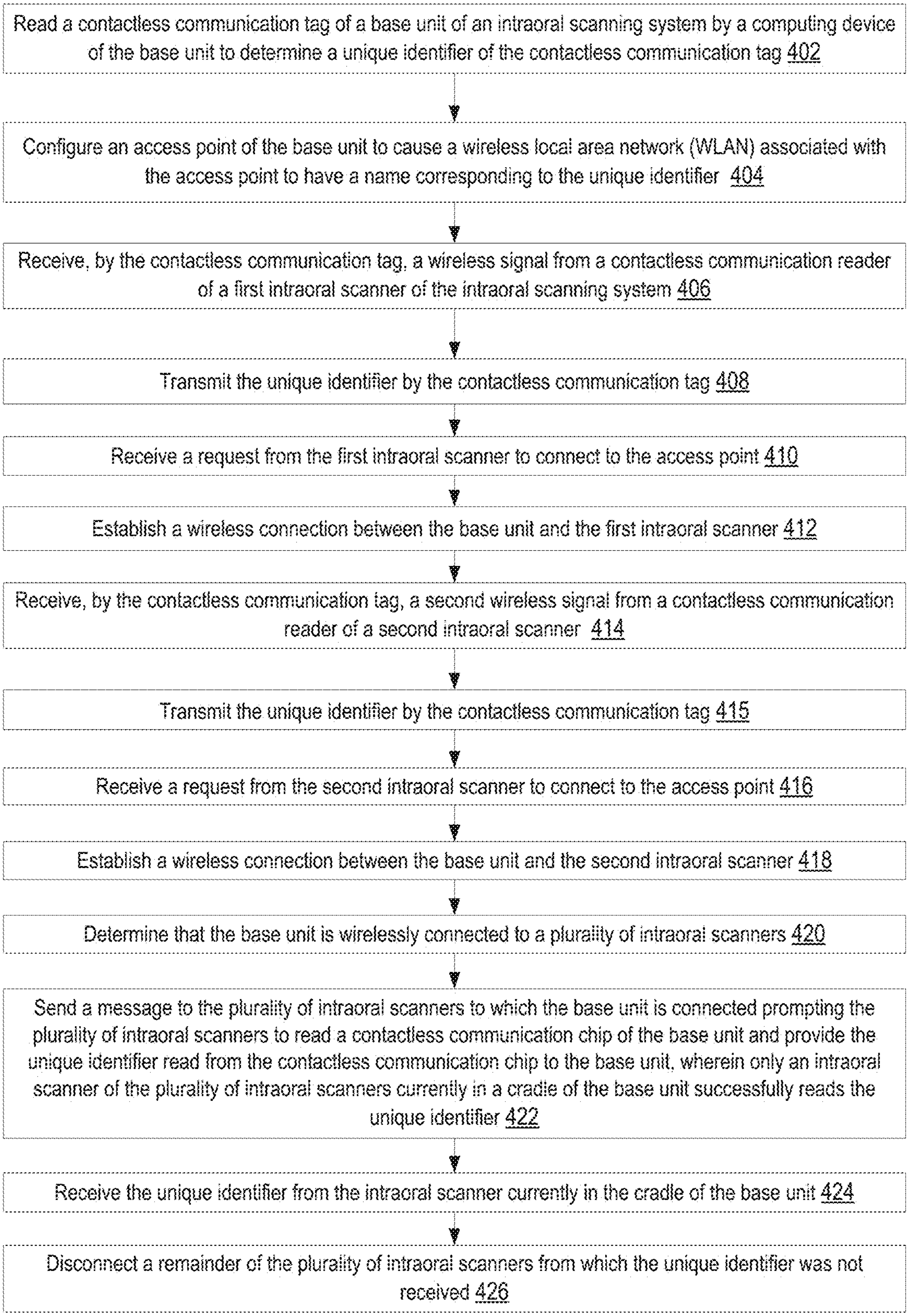
FIG. 4 illustrates a flow diagram for a method performed by a base unit to pair with an intraoral scanner of an intraoral scanning system, in accordance with embodiments of the present disclosure.
Figure 5:
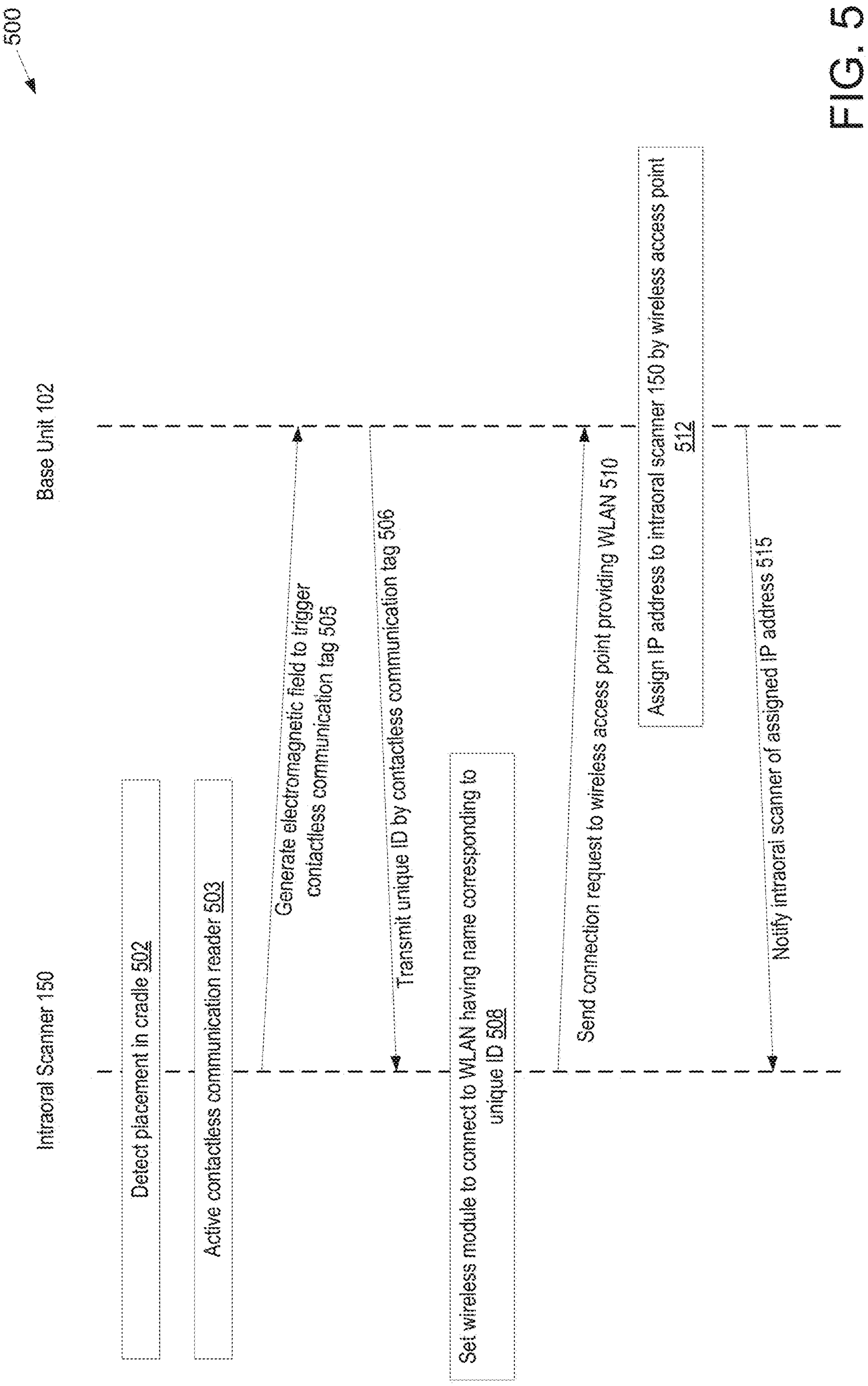
FIG. 5 is a sequence diagram illustrating pairing of an intraoral scanner to a base unit of an intraoral scanning system, in accordance with embodiments of the present disclosure.

FIGS. 3-5 illustrate methods and sequence diagrams related to pairing an intraoral scanner to a base unit, according to embodiments. Operations of the methods may be performed by a processing logic that may comprise hardware (e.g., circuitry, dedicated logic, programmable logic, microcode, etc.), software (e.g., instructions run on a processing device to perform hardware simulation), or a combination thereof. In one embodiment, at least some operations of the methods are performed by an intraoral scanning system that includes an intraoral scanner and a computing device wirelessly connected to the intraoral scanner.

For simplicity of explanation, the methods are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

FIG. 3 illustrates a flow diagram for a method 300 performed by an intraoral scanner to pair with a base unit of an intraoral scanning system, in accordance with embodiments of the present disclosure. In some embodiments, each of the operations of method 300 are performed automatically without user input.

At block 301 of method 300, an intraoral scanner receives a wireless signal provided by a base unit, wherein the wireless signal comprises a unique identifier (ID) and corresponds to a first wireless protocol. In one embodiment, the first wireless communication protocol is NFC or RFID. In one embodiment, at block 302 a contactless communication reader of the intraoral scanner may generate an electromagnetic field. The electromagnetic field may cause a contactless communication tag of the base unit to output a wireless signal comprising the unique identifier. At block 304, the intraoral scanner may receive the wireless signal provided by the contactless communication tag or device of the base unit.

In some embodiments, operations 301-304 are performed while the intraoral scanner is turned on. In some embodiments, operations 301-304 are performed while the intraoral scanner is turned off. In such instances, a control module of the intraoral scanner may be powered on even when the intraoral scanner is turned off. The control module may determine when to activate the contactless communication reader of the intraoral scanner, and may cause the contactless communication reader to read the contactless communication tag or device. At block 306, the intraoral scanner (e.g., the control module) may then store the received unique ID in a memory. The unique ID may then be retrieved from memory and used to connect to the base unit once the intraoral scanner is turned on.

In some embodiments, the intraoral scanner may have multiple different modes of operation. A first mode of operation may be an off mode, in which the intraoral scanner is turned off except for a control module of the intraoral scanner. A second mode of operation may be an inactive mode, which may occur when the intraoral scanner is in a powered on state but an intraoral scan application of the base unit is not running. A third mode may be a scanning mode, which may occur when the intraoral scanner is powered on and an intraoral scan application is active on the base unit.

The association process between the intraoral scanner and base unit is an automatic process that may be initiated by the control module when the wand is in the off mode. The control module may always be in an operational state even if the intraoral scanner is in the powered off state from a doctor's point of view. In this power off mode the control module may follow a standard contactless communication (e.g., NFC reader) protocol that triggers reading of a contactless communication tag (e.g., NFC tag) if it is close enough. This ensures that if the intraoral scanner is moved from one base unit to another during a non-operational state the intraoral scanner is automatically associated with the last base unit. When the intraoral scanner is powered on by the doctor, the control module may lose control over the association process, and a wireless module of the intraoral scanner may establish a connection to the wireless access point according to a last associated unique ID. In some embodiments, the control module causes power to be supplied to the wireless module while the intraoral scanner is turned off to enable a wireless connection to be established between scanner and the base unit before the scanner is turned on.

As mentioned, the inactive mode describes the mode when the intraoral scanner is in a power on state but the intraoral scanning application on the base unit is still closed. This may occur, for example, when a doctor finishes scanning a patient and closes the scanning application. In this mode, the intraoral scanner can be moved from one base unit to another. A controller or processor of the intraoral scanner may initiate a timer that will trigger association similar to the process described with reference to the off mode. In inactive mode, the connection to a wireless access point (AP) may exist. Accordingly, upon a new association of the intraoral scanner to a new base unit, the wireless connection that intraoral scanner may switch to another wireless AP of the new base unit according to a new associated unique ID associated with a contactless communication tag of the new base unit. When the intraoral scanner is connected to any wireless AP, it may start to run a pairing application in the background. The pairing application may listen for a wireless a AP request for a current ID and send the unique ID back to wireless AP in response.

One or more rules may be used to determine when to activate the contactless communication reader. The same or different rules may be used when the intraoral scanner is turned on and when the intraoral scanner is turned off. Any of the following rules may apply when the intraoral scanner is turned on and/or when the intraoral scanner is turned off. In one embodiment, the contactless communication reader has a default powered on state. IN one embodiment, the contactless communication reader is periodically activated. In one embodiment, the control module of the intraoral scanner includes one or more rules for determining when to power on the contactless communication reader. Based on these rules, the control module may determine whether the intraoral scanner satisfies one or more criteria of the one or more rules, and may activate the contactless communication reader responsive to determining that the one or more criteria are satisfied. In one embodiment, control module activates the contactless communication reader responsive to determining that the intraoral scanner has been still for a threshold amount of time. In one embodiment, the control module activates the contactless communication reader responsive to determining that the intraoral scanner has been still at a particular orientation (e.g., angle with respect to gravity) that is an orientation that the intraoral scanner has when placed in a cradle of the base unit. In one embodiment, the cradle for the base unit includes a wireless charger or a wired charger. In one embodiment, the control module detects when the intraoral scanner is charging, and powers on the contactless communication reader responsive to determining that the intraoral scanner is charging. In some embodiments, once the unique ID is received, the control module powers off the contactless communication reader.

In one embodiment, at block 308 the intraoral scanner is turned on (e.g., if the intraoral scanner was turned off at blocks 302-306).

At block 310, the intraoral scanner establishes a wireless connection with the base unit using the unique identifier. The wireless connection is established using a second wireless communication protocol different from the first wireless communication protocol. In one embodiment, the second wireless communication protocol is a wireless local area network (WLAN) protocol. In one embodiment, the second wireless communication protocol is Wi-Fi. In one embodiment, the operations of block 310 are performed while the intraoral scanner is turned off.

At block 312, the intraoral scanner may begin generating a plurality of intraoral scans of a patient's dental arch (e.g., may begin performing intraoral scanning). At block 314, the intraoral scanner may wirelessly transmit the intraoral scans to the base unit over the established wireless connection between the intraoral scanner and the base unit. The base unit may then store the intraoral scans and/or may use the intraoral scans to generate a 3D surface and/or a 3D model of the patient's dental arch.

At a later time the intraoral scanner may be moved to a different location, and may be positioned proximate to a second base unit (e.g., may be placed in a cradle of the second base unit). Responsive to such action, at block 316 the intraoral scanner may receive a second wireless signal provided by the second base unit. The second wireless signal may include a second unique ID associated with the second base unit, and may be sent according to the first wireless communication protocol. For example, the second base unit may include a second contactless communication tag that has a different unique ID than the unique ID of the contactless communication tag of the first base unit. At block 318, the intraoral scanner may establish a new wireless connection with the second base unit using the second unique ID. The new wireless connection may be established according to the second wireless communication protocol. Establishing the wireless connection to the second base unit may cause the intraoral scanner to lose its wireless connection to the first base unit in embodiments.

FIG. 4 illustrates a flow diagram for a method 400 performed by a base unit to pair with an intraoral scanner of an intraoral scanning system, in accordance with embodiments of the present disclosure. In some embodiments, some or all of the operations of method 400 are performed automatically without user input.

At block 402 of method 400, a computing device of a base unit may read a contactless communication tag of the base unit (e.g., embedded in a cradle of the base unit). For example, the computing device may have a connection (e.g., a wired connection) to the contactless communication tag, and via the wired connection may read the contact less communication tag to determine a unique ID of the contactless communication tag. At block 404, the base unit may configure an access point of the base unit to cause a WLAN associated with the access point to have a name corresponding to the unique ID. In one embodiment, the operations of blocks 402-404 are performed once (e.g., at a factory) or responsive to an input to perform configuration.

At block 406, a contactless communication tag of the base unit may receive a wireless signal (e.g., an electromagnetic field) from a contactless communication reader of a first intraoral scanner. At block 408, the contactless communication tag may then transmit (e.g., broadcast) the unique ID of the contactless communication tag.

At block 410, the base unit receives a request from the first intraoral scanner to connect to the access point that is set to provide the WLAN having the name corresponding to the unique ID. At block 412, the access point establishes a wireless connection between the base unit and the first intraoral scanner.

At block 414, the contactless communication tag of the base unit may receive a second wireless signal (e.g., an electromagnetic field) from a contactless communication reader of a second intraoral scanner. At block 415, the contactless communication tag may then transmit (e.g., broadcast) the unique ID of the contactless communication tag.

At block 416, the base unit may receive a second request from the second intraoral scanner to connect to the access point that is set to provide the WLAN having the name corresponding to the unique ID. At block 418, the access point may establish a wireless connection between the base unit and the second intraoral scanner.

In some instances, the base unit may be connected to multiple intraoral scanners. In such instances, the base unit may perform one or more operations to determine which of the intraoral scanners it should be connected with and to disconnect the other intraoral scanners.

In one embodiment, at block 402 the base unit sends a message to a plurality of intraoral scanners wirelessly connected to the intraoral scanner. The message may be an instruction for the intraoral scanners to activate their contactless communication readers and read a unique ID of a contactless communication tag of the base unit, and to then provide the unique ID to the base unit. Only an intraoral scanner that is within a minimum range for a contactless communication protocol will be able to read the unique ID from the contactless communication tag or device of the base unit. For example, an intraoral scanner in a cradle of the base unit may be the only intraoral scanner able to read the unique ID from the contactless communication tag or device.

At block 424, the base unit receives the unique ID from the intraoral scanner currently in the cradle of the base unit (or otherwise within range of the contactless communication protocol). At block 426, the base unit then disconnects a remainder of the plurality of intraoral scanners that were not able to provide the base unit with the unique ID.

FIG. 5 is a sequence diagram 500 illustrating pairing of an intraoral scanner 150 to a base unit 102 of an intraoral scanning system, in accordance with embodiments of the present disclosure. In one embodiment, at block 502 the intraoral scanner detects placement in a cradle. In one embodiment, the intraoral scanner detects placement in the cradle based on a lack of motion (e.g., as detected by an IMU or accelerometer), based on detecting the cradle at a particular orientation or angle (e.g., as detected by an IMU or accelerometer), based on detecting that the intraoral scanner is being charged, and so on. Responsive to detecting that the intraoral scanner 150 is in the cradle, at block 503 the intraoral scanner may activate a contactless communication reader of the intraoral scanner.

At block 505, the intraoral scanner generates an electromagnetic field to trigger a contactless communication tag of the base unit. The intraoral scanner 150 briefly establishes a wireless connection with the base unit (e.g., via inductive coupling), and at block 506 the base unit transmits a unique ID. The unique ID may be a unique ID of the contactless communication tag, which may output the unique ID responsive to the electromagnetic field and/or brief wireless connection with the intraoral scanner 150.

At block 508, the intraoral scanner sets a wireless module to connect to a WLAN having a name corresponding to the unique ID. At block 510, the intraoral scanner sends a connection request to a wireless access point of the base unit that provides the WLAN. At block 512, the access point of the base unit may assign an IP address to the intraoral scanner (e.g., for a Wi-Fi connection). At block 515, the base unit may notify the intraoral scanner of the assigned IP address. The intraoral scanner 150 and base unit 102 may then have a persistent wireless connection (e.g., may be paired) until the wireless connection is terminated.

In some instances, a wireless connection between an intraoral scanner 150 and base unit 102 may be interrupted. For example, the intraoral scanner 150 may lose its connection to the base unit 102 if it is moved out of range of wireless communication protocol associated with the wireless connection, or if the intraoral scanner and/or base unit are powered off. In such instances, the intraoral scanner may attempt to automatically reestablish a wireless connection with a last base unit that it was connected to. For example, the intraoral scanner 150 may save a unique ID that corresponds to a name of a WLAN that it most recently connected to in memory, and may use that unique ID to establish a new wireless connection to the base unit.

In some embodiments, intraoral scanner 150 may provide one or more indications that it is not connected to a base unit and/or that it does not have in memory or storage any entry for a base unit to which it has previously connected. The indications may include, for example, a visual and/or audio indication. In some embodiments, the intraoral scanner 150 includes a screen (e.g., a touchscreen). The screen may output an icon and/or text notifying a user that the intraoral scanner is not connected to a base unit and/or is not associated with any base unit. Additionally, or alternatively, a base unit may output a visual and/or audio indication that the base unit is not associated with and/or connected with any intraoral scanners.

In some embodiments, the wireless access point and contactless communication tag of a base unit are hardwired in the base unit and cannot be removed from the base unit or replaced. In such embodiments, the unique ID of the base unit and the name of the WLAN provided by the access point are constant. In other embodiments, the access point and/or contactless communication tag may be replaced for a base unit. In such embodiments, the access point should be updated after changing of the access point and/or of the contactless communication tag to cause the access point to use a network name (e.g., SSID) that corresponds to the unique ID of the contactless communication tag.

Figure 6:
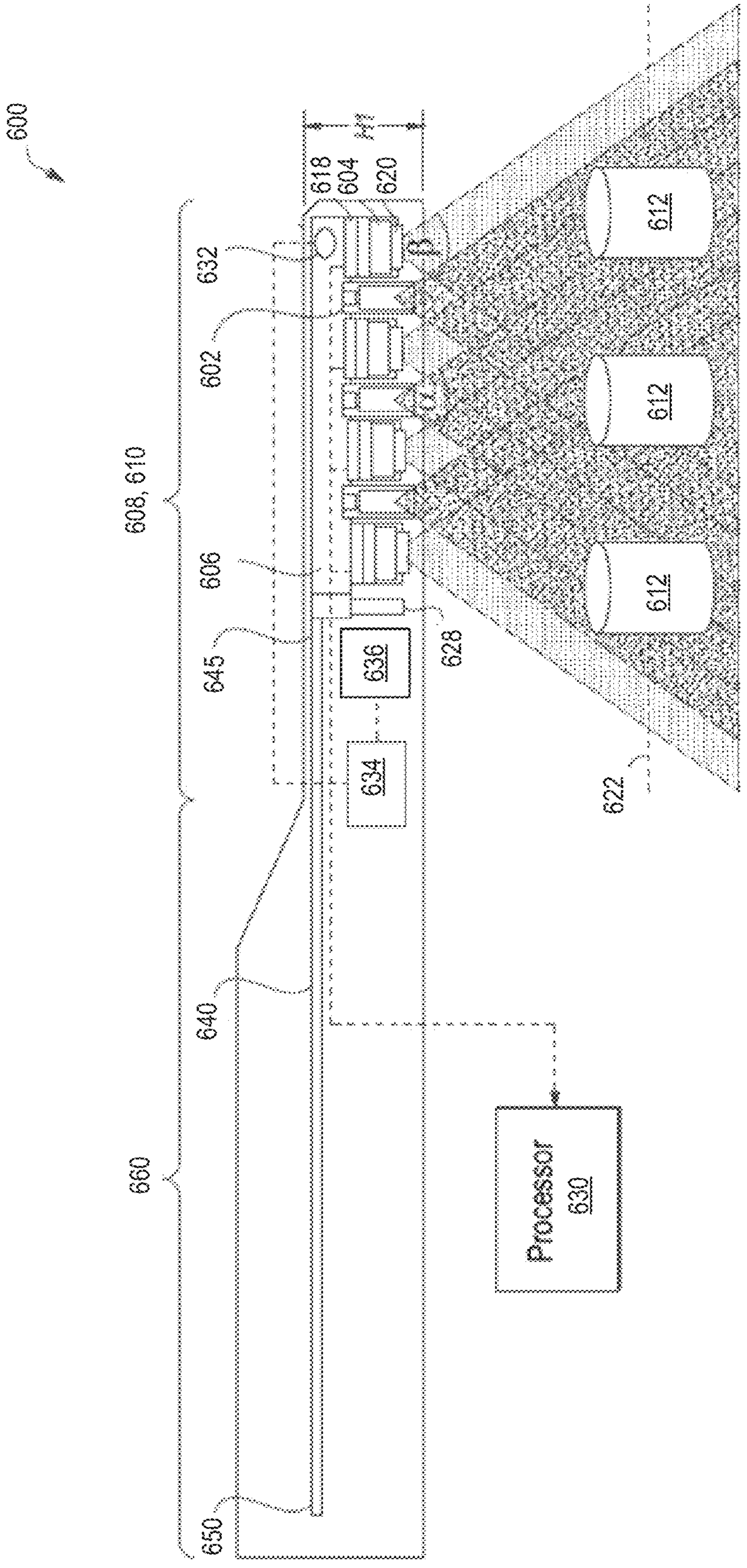
FIG. 6 illustrates an example intraoral scanner, in accordance with embodiments of the present disclosure.

Reference is now made to FIG. 6, which is a schematic illustration of an intraoral scanner 600 comprising an elongate handheld wand (e.g., a body with a probe at one end of the body), in accordance with some applications of the present disclosure. The intraoral scanner 600 may include a wireless module (not shown), a contactless communication reader (not shown), and/or other components discussed herein disposed in a body of the intraoral scanner 600. The intraoral scanner 600 may correspond to intraoral scanner 150 of FIGS. 1-5 in embodiments. Intraoral scanner 600 includes a plurality of structured light projectors 602 and a plurality of cameras 604 that are coupled to a rigid structure 606 disposed within a probe 608 at a distal end 610 of the body of the intraoral scanner 600. In some applications, during an intraoral scanning procedure, probe 608 is inserted into the oral cavity of a subject or patient.

For some applications, structured light projectors 602 are positioned within probe 608 such that each structured light projector 602 faces an object 612 outside of intraoral scanner 600 that is placed in its field of illumination, as opposed to positioning the structured light projectors in a proximal end of the handheld wand and illuminating the object by reflection of light off a mirror and subsequently onto the object. Alternatively, the structured light projectors may be disposed at a proximal end of the handheld wand. Similarly, for some applications, cameras 604 and/or other optical sensors are positioned within probe 608 such that each camera 604 faces an object 612 outside of intraoral scanner 600 that is placed in its field of view, as opposed to positioning the cameras in a proximal end of the intraoral scanner and viewing the object by reflection of light off a mirror and into the camera. This positioning of the projectors and the cameras within probe 608 enables the scanner to have an overall large field of view while maintaining a low profile probe. Alternatively, the cameras may be disposed in a proximal end of the handheld wand.

In some applications, cameras 604 each have a large field of view β (beta) of at least 45 degrees, e.g., at least 70 degrees, e.g., at least 80 degrees, e.g., 85 degrees. In some applications, the field of view may be less than 120 degrees, e.g., less than 100 degrees, e.g., less than 90 degrees. In one embodiment, a field of view β (beta) for each camera is between 80 and 90 degrees, which may be particularly useful because it provided a good balance among pixel size, field of view and camera overlap, optical quality, and cost. Cameras 604 may include an image sensor 618 and objective optics 620 including one or more lenses. To enable close focus imaging, cameras 604 may focus at an object focal plane 622 that is located between 1 mm and 30 mm, e.g., between 4 mm and 24 mm, e.g., between 5 mm and 11 mm, e.g., 9 mm-10 mm, from the lens that is farthest from the sensor. In some applications, cameras 604 may capture images at a frame rate of at least 30 frames per second, e.g., at a frame of at least 75 frames per second, e.g., at least 100 frames per second. In some applications, the frame rate may be less than 200 frames per second.

A large field of view achieved by combining the respective fields of view of all the cameras may improve accuracy due to reduced amount of image stitching errors, especially in edentulous regions, where the gum surface is smooth and there may be fewer clear high resolution 3D features. Having a larger field of view enables large smooth features, such as the overall curve of the tooth, to appear in each image frame, which improves the accuracy of stitching respective surfaces obtained from multiple such image frames.

Similarly, structured light projectors 602 may each have a large field of illumination a (alpha) of at least 45 degrees, e.g., at least 70 degrees. In some applications, field of illumination a (alpha) may be less than 120 degrees, e.g., than 100 degrees.

For some applications, in order to improve image capture, each camera 604 has a plurality of discrete preset focus positions, in each focus position the camera focusing at a respective object focal plane 622. Each of cameras 604 may include an autofocus actuator that selects a focus position from the discrete preset focus positions in order to improve a given image capture. Additionally or alternatively, each camera 604 includes an optical aperture phase mask that extends a depth of focus of the camera, such that images formed by each camera are maintained focused over all object distances located between 1 mm and 30 mm, e.g., between 4 mm and 24 mm, e.g., between 5 mm and 11 mm, e.g., 9 mm-10 mm, from the lens that is farthest from the sensor.

In some applications, structured light projectors 602 and cameras 604 are coupled to rigid structure 606 in a closely packed and/or alternating fashion, such that (a) a substantial part of each camera's field of view overlaps the field of view of neighboring cameras, and (b) a substantial part of each camera's field of view overlaps the field of illumination of neighboring projectors. Optionally, at least 20%, e.g., at least 50%, e.g., at least 75% of the projected pattern of light are in the field of view of at least one of the cameras at an object focal plane 622 that is located at least 4 mm from the lens that is farthest from the sensor. Due to different possible configurations of the projectors and cameras, some of the projected pattern may never be seen in the field of view of any of the cameras, and some of the projected pattern may be blocked from view by object 612 as the scanner is moved around during a scan.

Rigid structure 606 may be a non-flexible structure to which structured light projectors 602 and cameras 604 are coupled so as to provide structural stability to the optics within probe 608. Coupling all the projectors and all the cameras to a common rigid structure helps maintain geometric integrity of the optics of each structured light projector 602 and each camera 604 under varying ambient conditions, e.g., under mechanical stress as may be induced by the subject's mouth. Additionally, rigid structure 606 helps maintain stable structural integrity and positioning of structured light projectors 602 and cameras 604 with respect to each other.

For some applications, there is at least one uniform light projector 628 (which may be an unstructured light projector that projects light across a range of wavelengths) coupled to rigid structure 606. Uniform light projector 628 may transmit white light onto object 612 being scanned. At least one camera, e.g., one of cameras 604, captures two-dimensional color images of object 612 using illumination from uniform light projector 628. Light reflecting off of the object 612 may enter the scanner head and be received by the cameras. The cameras may then generate intraoral scan data based on the received light. The wireless communication module may wirelessly send the intraoral scan data to a computing device in embodiments.

A processor or processing device 630 of the computing device may run a surface reconstruction algorithm that may use detected patterns (e.g., dot patterns) projected onto object 612 to generate a 3D surface of the object 612. In some embodiments, the processor 630 may combine at least one 3D scan captured using illumination from structured light projectors 602 with a plurality of intraoral 2D images captured using illumination from uniform light projector 628 in order to generate a digital three-dimensional image of the intraoral three-dimensional surface. Using a combination of structured light and uniform illumination enhances the overall capture of the intraoral scanner and may help reduce the number of options that processor 630 needs to consider when running a correspondence algorithm used to detect depth values for object 612. In one embodiment, the intraoral scanner and correspondence algorithm described in U.S. application Ser. No. 16/446,181, filed Jun. 19, 2019, is used. U.S. application Ser. No. 16/446,181, filed Jun. 19, 2019, is incorporated by reference herein in its entirety. In embodiments, processor 630 may be a processor of computing device 105 of FIG. 1. Alternatively, processor 630 may be a processor integrated into the intraoral scanner 600.

For some applications, all data points taken at a specific time are used as a rigid point cloud, and multiple such point clouds are captured at a frame rate of over 10 captures per second. The plurality of point clouds are then stitched together using a registration algorithm, e.g., iterative closest point (ICP), to create a dense point cloud. A surface reconstruction algorithm may then be used to generate a representation of the surface of object 612.

For some applications, at least one temperature sensor 632 is coupled to rigid structure 606 and measures a temperature of rigid structure 606. Temperature control circuitry 634 disposed within intraoral scanner 600 (a) receives data from temperature sensor 632 indicative of the temperature of rigid structure 606 and (b) activates a temperature control unit 636 in response to the received data. Temperature control unit 636, e.g., a PID controller, keeps probe 608 at a target temperature (e.g., between 35 and 43 degrees Celsius, between 37 and 41 degrees Celsius, etc.). Keeping probe 608 above 35 degrees Celsius, e.g., above 37 degrees Celsius, reduces fogging of the glass surface of intraoral scanner 600, through which structured light projectors 602 project and cameras 604 view, as probe 608 enters the oral cavity, which is typically around or above 37 degrees Celsius. Keeping probe 608 below 43 degrees, e.g., below 41 degrees Celsius, prevents discomfort or pain.

In some embodiments, heat may be drawn out of the probe 608 via a heat conducting element 640, e.g., a heat pipe, that is disposed within intraoral scanner 600, such that a distal end 645 of heat conducting element 640 is in contact with rigid structure 606 and a proximal end 650 is in contact with a proximal end 660 of intraoral scanner 600. Heat is thereby transferred from rigid structure 606 to proximal end 660 of intraoral scanner 600. Alternatively or additionally, a fan disposed in a handle region of intraoral scanner 600 may be used to draw heat out of probe 608.

In one embodiment, intraoral scanner 150 corresponds to the intraoral scanner described in U.S. application Ser. No. 16/910,042, filed Jun. 23, 2020 and entitled "Intraoral 3D Scanner Employing Multiple Miniature Cameras and Multiple Miniature Pattern Projectors", which is incorporated by reference herein. In one embodiment, intraoral scanner 150 corresponds to the intraoral scanner described in U.S. application Ser. No. 16/446,181, filed Jun. 19, 2019 and entitled "Intraoral 3D Scanner Employing Multiple Miniature Cameras and Multiple Miniature Pattern Projectors", which is incorporated by reference herein.

In some embodiments, intraoral scanner 600 includes a touchscreen (not shown) disposed on the body of the intraoral scanner 600. The touchscreen may be configured to output a plurality of virtual buttons, to detect a touch input associated with a virtual button of the plurality of virtual buttons, and to provide a signal associated with the touch input of the virtual button to the processor of the computing device. In some embodiments, intraoral scanner 600 may receive an input from the computing device indicating a current mode of an intraoral scan application. Intraoral scanner 600 may then determine the plurality of virtual buttons to output on the touchscreen based on the current mode of the intraoral scan application and/or based on past inputs. Alternatively, the computing device may determine what virtual buttons are to be displayed on the touchscreen, and may provide data on what is to be displayed on the touchscreen to intraoral scanner 600.

In some embodiments an intraoral scanner that performs confocal focusing to determine depth information may be used.

Figure 7:
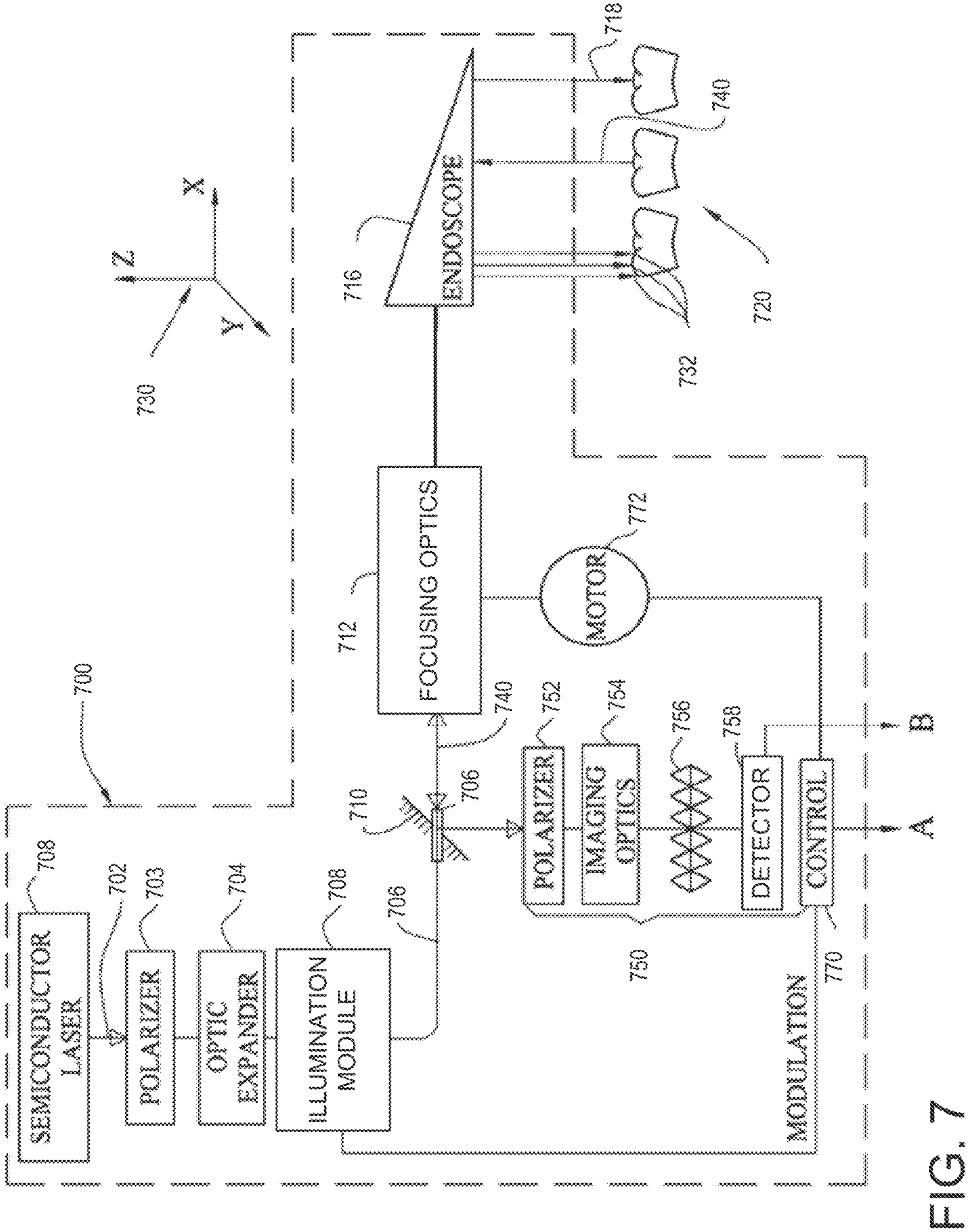
FIG. 7 illustrates another example intraoral scanner, in accordance with embodiments of the present disclosure.

FIG. 7 illustrates a functional block diagram of an intraoral scanner 700 according to one embodiment. Intraoral scanner 700 may correspond to intraoral scanner 150 of FIGS. 1-5 in embodiments. Together, the intraoral scanner 700 and a computing device (e.g., computing device 105) may form a system for generating three dimensional surfaces and/or models of scanned intraoral objects (e.g., an intraoral scanning system). In one embodiment, the intraoral scanner is a confocal intraoral scanner. In one embodiment, intraoral scanner 700 includes a touchscreen, a wireless communication module, a contactless communication reader, and so on as discussed above.

In one embodiment intraoral scanner 700 includes a body comprising a probe at one end of the body. The probe includes a scanner head. The probe may include, for example, an endoscope 716. Intraoral scanner 700 includes a semiconductor laser unit (illumination module) 708 in the body that emits focused light (e.g., a focused light beam), as represented by arrow 702. The light 702 passes through a polarizer 703. Polarizer 703 polarizes the light beam passing through polarizer 703. Alternatively, polarizer 703 may be omitted in some embodiments. The light then enters into an optic expander 704 in the body that improves a numerical aperture of the light 702. The light 702 then passes through an illumination module 708 in the body, which may split the light 702 into an array of incident light beams 706, represented here, for ease of illustration, by a single line. The illumination module 708 may be, for example, a grating or a micro lens array that splits the light 702 into an array of light beams 706. In one embodiment, the array of light beams 706 is an array of telecentric light beams. Alternatively, the array of light beams may not be telecentric.

The intraoral scanner 700 further includes a unidirectional mirror or beam splitter (e.g., a polarizing beam splitter) 710 in the body that passes the array of light beams 706. A unidirectional mirror 710 allows transfer of light from the semiconductor laser 708 through to downstream optics, but reflects light travelling in the opposite direction. A polarizing beam splitter allows transfer of light (e.g., light beams) having a particular polarization and reflects light beams having a different (e.g., opposite) polarization. In one embodiment, the unidirectional mirror or beam splitter 710 has a small central aperture. The small central aperture may improve a measurement accuracy of the intraoral scanner 700. In one embodiment, as a result of a structure of the unidirectional mirror or beam splitter 710, the array of light beams will yield a light annulus on an illuminated area of an imaged object as long as the area is not in focus. Moreover, the annulus will become a completely illuminated spot once in focus. This ensures that a difference between measured intensities of out-of-focus points and in-focus points will be larger.

Along an optical path of the array of light beams after the unidirectional mirror or beam splitter 710 are focusing optics 712 in the body, and an endoscopic probing member 46 at one end of the body. In one embodiment, the focusing optics are confocal focusing optics. Additionally, a quarter wave plate may be disposed along the optical path after the unidirectional mirror or beam splitter 710 to introduce a certain polarization to the array of light beams. In some embodiments this may ensure that reflected light beams will not be passed through the unidirectional mirror or beam splitter 710. Focusing optics 712 may additionally include relay optics (not shown). Focusing optics 712 may or may not maintain the same magnification of an image over a wide range of distances in the Z direction, wherein the Z direction is a direction of beam propagation (e.g., the Z direction corresponds to an imaging axis that is aligned with an optical path of the array of light beams 706). The relay optics enable the intraoral scanner 700 to maintain a certain numerical aperture for propagation of the array of light beams 706.

The endoscopic probing member 716 may include a rigid, light-transmitting medium, which may be a hollow object defining within it a light transmission path or an object made of a light transmitting material, e.g. a glass body or tube. In one embodiment, the endoscopic probing member 716 include a prism such as a folding prism. At its end, the endoscopic probing member 716 may include a mirror of the kind ensuring a total internal reflection. Thus, the mirror may direct the array of light beams towards a teeth segment 720 or other intraoral object. The endoscope probing member 716 thus emits light 718 (e.g., an array of light beams), which impinges on to surfaces of the teeth section 720.

The light 718 (e.g., array of light beams) may be arranged in an X-Y plane, in the Cartesian frame 730, propagating along the Z axis. As the surface on which the incident light hits is an uneven surface, illuminated points or locations 732 are displaced from one another along the Z axis, at different (X, Y) locations. Thus, while a point at one location may be in focus of the focusing optics 712, points at other locations may be out-of-focus. Therefore, the light intensity of returned light (e.g., returned light beams) of the focused points will be at its peak, while the light intensity at other points will be off peak. Thus, for each illuminated point, multiple measurements of light intensity are made at different positions along the Z-axis. For each of such (X, Y) location, the derivative of the intensity over distance (Z) may be made, with the $Z_i$ yielding maximum derivative, $Z_0$, being the in-focus distance. As pointed out above, the incident light from the light 718 may form a light disk or a blurry image on the surface when out of focus and a complete light spot or a sharp image when in focus. Thus, the distance derivative will be larger when approaching in-focus position, increasing accuracy of the measurement.

The light scattered from each of the points may include a beam travelling initially in the Z axis along the opposite direction of the optical path traveled by the light beam 718. Each returned light beam in an array of returning light beams 740 may correspond to one of the incident light beams in array of light beams 706. Given the asymmetrical properties of unidirectional mirror or beam splitter 710, the returned light is reflected in the direction of detection optics 750 in the body.

The detection optics 750 may include a polarizer 752 that has a plane of preferred polarization oriented normal to the plane polarization of polarizer 703. Alternatively, polarizer 703 and polarizer 752 may be omitted in some embodiments. The array of returning light 740 (e.g., array of returning light beams) may pass through imaging optics 754 in one embodiment. The imaging optics 754 may include one or more lenses. Alternatively, the detection optics 750 may not include imaging optics 754. In one embodiment, the returning light 740 further passes through a matrix 756, which may be an array of pinholes. Alternatively, no matrix 756 is used in some embodiments. The returning light 740 is then directed onto a detector 758 in the body.

The detector 758 is an image sensor having a matrix of sensing elements each representing a pixel of the image. If matrix 756 is used, then each pixel further corresponds to one pinhole of matrix 756. In one embodiment, the detector is a charge coupled device (CCD) sensor. In one embodiment, the detector is a complementary metal-oxide semiconductor (CMOS) type image sensor. Other types of image sensors may also be used for detector 758. In one embodiment, the detector 758 detects light intensity at each pixel.

In one embodiment, detector 758 provides data to a computing device, such as computing device 75 of FIG. 1. Thus, each light intensity measured in each of the sensing elements of the detector 758, is then captured and analyzed.

Intraoral scanner 700 further includes a control module 770 in the body connected both to semiconductor laser 708 and a motor 772, voice coil or other translation mechanism. In one embodiment, control module 770 is or includes a field programmable gate array (FPGA) configured to perform control operations. Motor 772 is linked to focusing optics 712 for changing a focusing setting of confocal focusing optics 712. This may adjust the relative location of an imaginary flat or non-flat focal surface of focusing optics 742 along the Z-axis (e.g., in the imaging axis). Control module 770 may induce motor 772 to axially displace (change a location of) one or more lenses of the focusing optics 712 to change the focal depth of the imaginary flat or non-flat focal surface. In one embodiment, motor 772 or intraoral scanner 700 includes an encoder (not shown) that accurately measures a position of one or more lenses of the focusing optics 712. The encoder may include a sensor paired to a scale that encodes a linear position. The encoder may output a linear position of the one or more lenses of the focusing optics 712. The encoder may be an optical encoder, a magnetic encoder, an inductive encoder, a capacitive encoder, an eddy current encoder, and so on. After receipt of feedback that the location of the one or more lenses has changed, control module 770 may induce laser 708 to generate a light pulse.

Processing logic of the computing device may determine the relative intensity in each pixel of a received intraoral scan over the entire range of focal settings of focusing optics 712 from received intraoral scan data. Once a certain light point associated with a particular pixel is in focus, the measured intensity will be maximal for that pixel. Thus, by determining the Z, corresponding to the maximal light intensity or by determining the maximum displacement derivative of the light intensity, for each pixel, the relative position of each light point or spot along the Z axis can be determined for each pixel. Thus, data representative of the three-dimensional pattern of a surface in the teeth segment 720 or other intraoral object can be obtained.

Figure 8:
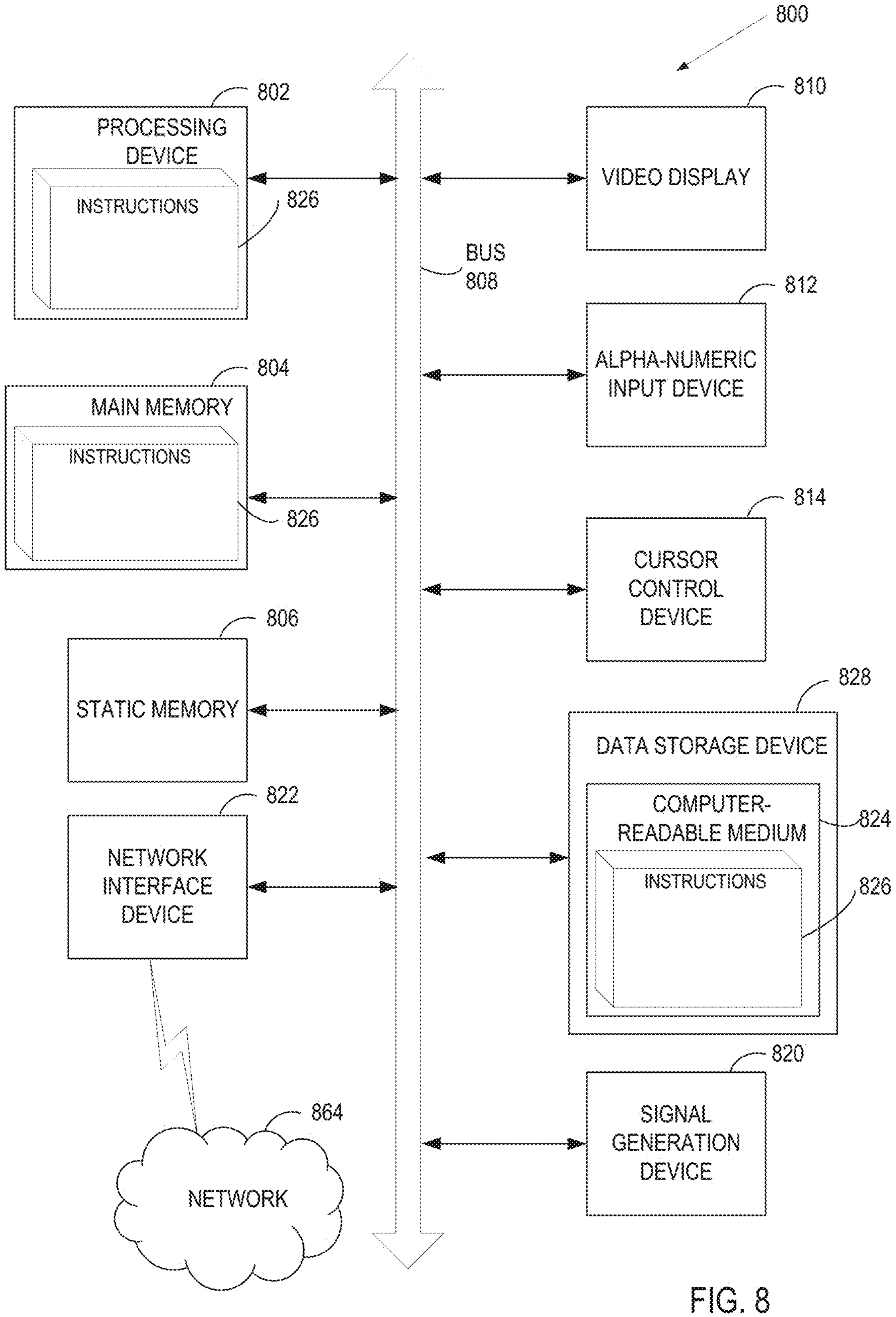
FIG. 8 illustrates a computing device, in accordance with embodiments of the present disclosure.

FIG. 8 illustrates a diagrammatic representation of a machine in the example form of a computing device 800 within which a set of instructions, for causing the machine to perform any one or more of the methodologies discussed herein, may be executed. In alternative embodiments, the machine may be connected (e.g., networked) to other machines in a local area network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet computer, a set-top box (STB), a personal digital assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein. In one embodiment, the computer device 800 corresponds to computing device 105 of FIG. 1.

The example computing device 800 includes a processing device 802, a main memory 804 (e.g., read-only memory (ROM), flash memory, dynamic random access memory (DRAM) such as synchronous DRAM (SDRAM), etc.), a static memory 806 (e.g., flash memory, static random access memory (SRAM), etc.), and a secondary memory (e.g., a data storage device 828), which communicate with each other via a bus 808.

Processing device 802 represents one or more general-purpose processors such as a microprocessor, central processing unit, or the like. More particularly, the processing device 802 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 802 may also be one or more special-purpose processing devices such as an application specific integrated circuit (ASIC), a field programmable gate array (FPGA), a digital signal processor (DSP), network processor, or the like. Processing device 802 is configured to execute the processing logic (instructions 826) for performing operations and steps discussed herein.

The computing device 800 may further include a network interface device 822 for communicating with a network 864. The computing device 800 also may include a video display unit 810 (e.g., a liquid crystal display (LCD) or a cathode ray tube (CRT)), an alphanumeric input device 812 (e.g., a keyboard), a cursor control device 814 (e.g., a mouse), and a signal generation device 820 (e.g., a speaker).

The data storage device 828 may include a machine-readable storage medium (or more specifically a non-transitory computer-readable storage medium) 824 on which is stored one or more sets of instructions 826 embodying any one or more of the methodologies or functions described herein. A non-transitory storage medium refers to a storage medium other than a carrier wave. The instructions 826 may also reside, completely or at least partially, within the main memory 804 and/or within the processing device 802 during execution thereof by the computer device 800, the main memory 804 and the processing device 802 also constituting computer-readable storage media.

The computer-readable storage medium 824 may also be used to store instructions for performing any of the operations described herein. The computer readable storage medium 824 may also store a software library containing methods for performing any of the operations described herein. While the computer-readable storage medium 824 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium other than a carrier wave (e.g., a non-transitory computer readable medium) that is capable of storing or encoding a set of instructions for execution by the machine and that cause the machine to perform any one or more of the methodologies of the present disclosure. The term "computer-readable storage medium" shall accordingly be taken to include, but not be limited to, solid-state memories, and optical and magnetic media.

It is to be understood that the above description is intended to be illustrative, and not restrictive. Many other embodiments will be apparent upon reading and understanding the above description. Although embodiments of the present disclosure have been described with reference to specific example embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

What is claimed is:

1. An intraoral scanning system comprising:

an intraoral scanner comprising one or more motion sensors; and a base unit comprising a computing device, a display, and a cradle for the intraoral scanner;

wherein:

responsive to a detected interaction between the intraoral scanner and the base unit, the intraoral scanner causes the base unit to wirelessly broadcast a unique identifier according to a first wireless communication protocol and the intraoral scanner receives the unique identifier;

the intraoral scanner is configured to use the unique identifier to establish a wireless connection with the base unit according to a second wireless communication protocol; and the base unit is configured to output a connection status indication on the display.

2. The intraoral scanning system of claim 1, wherein responsive to the intraoral scanner being powered on, the intraoral scanner establishes the wireless connection with the base unit.

3. The intraoral scanning system of claim 2, wherein a component of the intraoral scanner is configured to remain powered even while the intraoral scanner is turned off, and wherein the component of the intraoral scanner is configured to store the unique identifier in a memory.

4. The intraoral scanning system of claim 2, wherein after the intraoral scanner is powered on, the intraoral scanner is configured to:
generate a plurality of intraoral scans of a patient's dental arch; and
wirelessly transmit the plurality of intraoral scans to the base unit over the wireless connection.

5. The intraoral scanning system of claim 4, wherein the base unit is configured to:
generate a three-dimensional (3D) surface of at least a portion of the patient's dental arch based on the plurality of intraoral scans; and
output the 3D surface to the display of the base unit.

6. The intraoral scanning system of claim 1, wherein the first wireless communication protocol is a contactless communication protocol, wherein the intraoral scanner causes the base unit to broadcast the unique identifier by a contactless communication reader of the intraoral scanner generating an electromagnetic field that causes a contactless communication tag of the base unit to wirelessly broadcast the unique identifier, and wherein the second wireless communication protocol is a wireless local area network (WLAN) protocol.

7. The intraoral scanning system of claim 1, wherein the base unit further comprises a wireless access point that provides a wireless local area network (WLAN) associated with the unique identifier.

8. The intraoral scanning system of claim 7, wherein:
the cradle comprises a contactless communication chip,
the computing device is connected to the contactless communication chip via a wired connection through which the computing device is configured to receive the unique identifier from the contactless communication chip, and
the computing device is configured to set a name of the WLAN to match the unique identifier of the contactless communication chip.

9. The intraoral scanning system of claim 1, wherein the base unit comprises a wheeled cart.

10. The intraoral scanning system of claim 1, wherein:
the cradle comprises a contactless communication chip; and
the intraoral scanner comprises a contactless communication reader that is configured to read the unique identifier from the contactless communication chip.

11. The intraoral scanning system of claim 1, wherein the intraoral scanner is configured to establish the wireless connection with the base unit automatically without user input.

12. The intraoral scanning system of claim 1, wherein the intraoral scanner comprises a display, and wherein the display is configured to output a notice while the intraoral scanner is not connected to any base unit.

13. The intraoral scanning system of claim 1, wherein the display is configured to output a notice while the base unit is not connected to any intraoral scanner.

14. The intraoral scanning system of claim 1, wherein responsive to a determination by the base unit that it is connected to a plurality of intraoral scanners, the base unit is configured to:
send a message to the plurality of intraoral scanners to which the base unit is connected prompting the plurality of intraoral scanners to read a contactless communication chip of the base unit and provide the unique identifier read from the contactless communication chip to the base unit, wherein only an intraoral scanner of the plurality of intraoral scanners currently in the cradle of the base unit successfully reads the unique identifier;
receive the unique identifier from the intraoral scanner currently in the cradle of the base unit; and
disconnect a remainder of the plurality of intraoral scanners from which the unique identifier was not received.

15. A wireless intraoral scanner for an intraoral scanning system, comprising:
one or more motion sensors;
a contactless communication reader to read a unique identifier from a contactless communication tag of a base unit of the intraoral scanning system by generating an electromagnetic field that causes the contactless communication tag of the base unit to wirelessly broadcast the unique identifier according to a first wireless communication protocol; and
a wireless network interface module to receive the unique identifier from the contactless communication reader and use the unique identifier to establish a wireless connection, according to a second wireless communication protocol, with a wireless access point of the base unit that provides a wireless local area network (WLAN), wherein a name of the WLAN corresponds to the unique identifier.

16. The wireless intraoral scanner of claim 15, wherein responsive to the wireless intraoral scanner being powered on, the wireless intraoral scanner establishes the wireless connection with the wireless access point of the base unit.

17. The wireless intraoral scanner of claim 16, further comprising:
a control unit that remains powered even while the wireless intraoral scanner is turned off, wherein the control unit of the wireless intraoral scanner comprises a memory to store the unique identifier.

18. The wireless intraoral scanner of claim 16, wherein after the wireless intraoral scanner is powered on, the wireless intraoral scanner is configured to:
generate a plurality of intraoral scans of a patient's dental arch; and
wirelessly transmit the plurality of intraoral scans to the base unit over the wireless connection, wherein the base unit is configured to generate a three-dimensional (3D) surface of at least a portion of the patient's dental arch based on the plurality of intraoral scans and output the 3D surface to a display of the base unit.

19. The wireless intraoral scanner of claim 15, wherein:
the contactless communication reader of the wireless intraoral scanner is configured to read the contactless communication tag of the base unit responsive to the wireless intraoral scanner being placed in a cradle of the base unit.

20. The wireless intraoral scanner of claim 15, wherein the wireless intraoral scanner is configured to establish the wireless connection with the base unit automatically without user input.

21. The wireless intraoral scanner of claim 15, wherein the wireless intraoral scanner comprises a display, and wherein the display is configured to output a notice while the wireless intraoral scanner is not connected to any base unit.

22. A base unit for an intraoral scanning system, comprising:

a cradle comprising a contactless communication tag;

a wireless access point;

a display; and a computing device having a connection to the contactless communication tag, to the display, and to the wireless access point;

wherein the computing device is configured to:

read the contactless communication tag to determine a unique identifier of the contactless communication tag; and configure the wireless access point to cause a wireless local area network (WLAN) associated with the wireless access point to have a name corresponding to the unique identifier;

wherein the contactless communication tag is configured to receive a wireless signal from a contactless communication reader of a first intraoral scanner of the intraoral scanning system and broadcast the unique identifier;

wherein the computing device is configured to receive a request from the first intraoral scanner to connect to the wireless access point to establish a wireless connection between the base unit and the first intraoral scanner; and wherein the base unit is configured to output a connection status indication on the display.

23. The base unit of claim 22, wherein:

the contactless communication tag is further to receive a second wireless signal from a second contactless communication reader of a second intraoral scanner and subsequently broadcast the unique identifier; and the computing device is further to receive a request from the second intraoral scanner to connect to the wireless access point and to establish a wireless connection between the base unit and the second intraoral scanner.

24. The base unit of claim 22, wherein the base unit is configured to output a notice to the display until the base unit is connected to the first intraoral scanner.

25. The base unit of claim 22, wherein the computing device is further to:

determine that the base unit is wirelessly connected to a plurality of intraoral scanners;

send a message to the plurality of intraoral scanners to which the base unit is connected prompting the plurality of intraoral scanners to read a contactless communication chip of the base unit and provide the unique identifier read from the contactless communication chip to the base unit, wherein only an intraoral scanner of the plurality of intraoral scanners currently in the cradle of the base unit successfully reads the unique identifier;

receive the unique identifier from the intraoral scanner currently in the cradle of the base unit; and disconnect a remainder of the plurality of intraoral scanners from which the unique identifier was not received.

26. The base unit of claim 22, wherein the computing device has a wired connection to the contactless communication tag.

* * * * *